US005486597A

United States Patent [19]

Kalindjian et al.

[11] Patent Number: 5,486,597
[45] Date of Patent: Jan. 23, 1996

[54] TETRAPEPTIDE DERIVATIVES AND ANALOGUES

[75] Inventors: Sarkis B. Kalindjian, Banstead; Howard B. Broughton, Essex; Caroline M. R. Low, Croydon; Iain M. McDonald, Paddock Wood; Robert A. D. Hull, Tonbridge; Nigel P. Shankley, Nr. Edenbridge; Ildiko M. Buck, London; Katherine I. M. Steel, Harlow; Jonathan M. R. Davies, Fort Talbot, all of United Kingdom

[73] Assignee: James Black Foundation Limited, Dulwich, United Kingdom

[21] Appl. No.: 75,528

[22] PCT Filed: Dec. 17, 1991

[86] PCT No.: PCT/GB91/02249

§ 371 Date: Jun. 17, 1993

§ 102(e) Date: Jun. 17, 1993

[87] PCT Pub. No.: WO92/11284

PCT Pub. Date: Jul. 9, 1992

[30] Foreign Application Priority Data

Dec. 17, 1990 [GB] United Kingdom ............... 9027286
Nov. 1, 1991 [GB] United Kingdom ............... 9123231

[51] Int. Cl.⁶ ............... A61K 38/00; C07K 5/00; C07K 7/00; C07K 17/00
[52] U.S. Cl. ............... 530/331; 530/330
[58] Field of Search ............... 530/330, 331; 514/18

[56] References Cited

FOREIGN PATENT DOCUMENTS 0405506  1/1991  European Pat. Off.
90/06937  6/1990  WIPO.

OTHER PUBLICATIONS

Yabe et al., "Synthesis and Biological Activity of Tetragastrin Analogues modifying the Tryptophan Residue", *Chem. Pharm. Bull.* 25(10):2731–2734 (1977).

*Comprehensive Medicinal Chemistry*, vol. 3, pp. 932–936, Sammes et al. eds., Pergamon Press, Oxford (1990).

Shiosaki et al., "Development of CCK–Tetrapeptide Analogues as Potent and Selective CCK–A Receptor Agonists", *J. Med. Chem.* 33:2950–2952 (1990).

*Primary Examiner*—Jill Warden
*Assistant Examiner*—Sheela J. Huff
*Attorney, Agent, or Firm*—Foley & Lardner

[57] ABSTRACT

The C-terminal tetrapeptide of gastrin, Trp-Met-Asp-Phe-$NH_2$, possesses gastrin pharmacological activity. Replacement of the methionyl moiety in the gastrin tetrapeptide, or its analogs, with a naphthylalanyl group produces compounds which interact with gastrin and/or cholecystokinin receptors, but have reduced gastrin and/or cholecystokinin agonist activity. Such partial agonists or antagonists of gastrin and/or cholecystokinin provide useful therapeutic agents.

24 Claims, No Drawings

TETRAPEPTIDE DERIVATIVES AND ANALOGUES

This invention relates to tetrapeptide derivatives and analogues, and more particularly to tetrapeptide derivatives and analogues which are antagonists of the effects of gastrin and/or cholecystokinin (CCK) or which display gastrin and/or CCK like partial agonist activity. The invention also relates to methods for preparing such gastrin and/or CCK receptor ligands and to compounds which are useful as intermediates in such methods.

Gastrin and the CCK's are structurally-related neuropeptides which exist in gastrointestinal tissue and in the CNS (see Mutt V., *Gastrointestinal Hormones,* Glass G. B. J., ed., Raven Press, N.Y., p 169 and Nisson G., ibid, p. 127).

Several forms of gastrin are found including 34-, 17-, and 14-amino acid species with the minimum active fragment being the C-terminal tetrapeptide (TrpMetAspPhe-NH$_2$) which is reported in the literature to have full pharmacological activity (see Tracey H. J. and Gregory R. A., Nature (London), 1964, 204, 935). Much effort has been devoted to the synthesis of analogues of this tetrapeptide (and the N-protected derivative Boc-TrpMetAspPhe-NH$_2$) in an attempt to elucidate the relationship between structure and activity. Some 500 compounds were examined for agonist activity by Morley (Proc. Roy. Soc. B, 1968, 170, 97; J. Chem. Soc. (C), 1969, 809).

Gastrin is one of the three primary stimulants of gastric acid secretion. A number of gastrin antagonists have been proposed for various therapeutic applications, including the prevention of gastrin-related disorders, gastrointestinal ulcers, Zollinger-Ellison syndrome, antral G Cell hyperplasia and other conditions in which lowered gastrin activity is desirable. The hormone has also been shown to have a trophic action on cells in the stomach and so an antagonist may be expected to be useful in the treatment of cancers, particularly in the stomach.

Natural cholecystokinin is a 33 amino acid peptide (CCK-33), the C-terminal 5 amino acids of which are identical to those of gastrin. Also found naturally is the C-terminal octapeptide (CCK-8) of CCK-33.

The cholecystokinins are reported to be important in the regulation of appetite. They stimulate intestinal motility, gall bladder contraction, pancreatic enzyme secretion, and are known to have a trophic action on the pancreas. They also inhibit gastric emptying and have various effects in the CNS. Possible therapeutic uses for cholecystokinin antagonists include the control of appetite disorders such as anorexia nervosa, and the treatment of pancreatic inflammation, biliary tract disease and various psychiatric disorders. Other possible uses are in the potentiation of opiate (e.g. morphine) analgesia, and in the treatment of cancers, especially of the pancreas. Moreover, ligands for cholecystokinin receptors in the brain (so-called CCK$_B$ receptors) have been claimed to possess anxiolytic activity.

Natural hormones and hormone-like drugs (agonists) can bind to their specific receptors and then fully activate receptor-mediated effects (efficacy). Antagonists are compounds which have no efficacy but retain affinity. Therefore, when receptors are occupied by antagonists they can completely suppress the effects of the corresponding hormone. Partial agonists have only a relative loss of efficacy. Given alone they cannot produce as high a maximum effect as the hormone. Thus a partial agonist which is occupying all the receptors and producing, say, only 20% of the hormone's maximum effect will, therefore, antagonise the hormone's effect at all levels above 20%. Partial agonists are, therefore, potentially useful drugs for two reasons: (1) they antagonise high levels of hormonal activity but set a lower bound to the degree of antagonism—they cannot totally suppress natural hormone activity at any dose level and (2) they can produce tissue-selective antagonism where the receptor density is not uniformly expressed in different tissues. (See Kenakin T. P. and Beek D., *J. Pharmac. Exp. Ther,* 1980, 213, 406 and Black J. W. and Leff P., Proc. R. Soc. Lond. B, 1983, 220, 141).

The present invention is based on the discovery that replacement of the methionyl moiety in Boc-TrpMetAsp-Phe-NH$_2$ and its analogues, by a naphthylalanyl group, results in compounds which interact with gastrin and/or cholecystokinin receptors but which possess reduced gastrin and/or cholecystokinin agonist activity, and may have antagonist activity. According to the present invention, therefore, there are provided compounds of the formula:

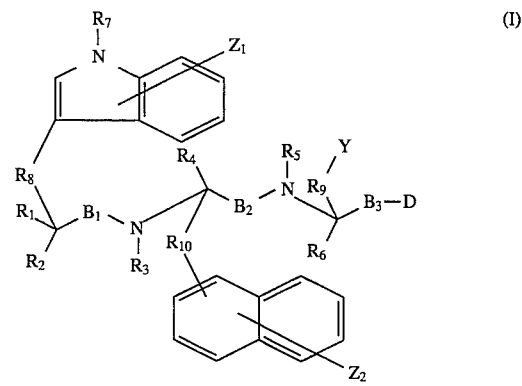

(I)

wherein R$_1$ is H or

R$_2$, R$_3$, R$_4$, R$_5$, and R$_6$ are independently H or methyl,

R$_7$ is H, methyl, ethyl, benzyl or formyl,

R$_8$ and R$_{10}$ are independently C$_1$ to C$_3$ alkylene or are absent,

R$_9$ is C$_1$ to C$_3$ alkylene or is linked to R$_6$ to form a 3- to 6-membered cycloalkyl group or is absent R$_{11}$ is an N-blocking group and R$_{12}$ is H or methyl, or R$_{11}$ and R$_{12}$ are linked to form an N-blocking group B$_1$, B$_2$ and B$_3$ are independently —CH$_2$— or a carbonyl group, Y is —CO$_2$H, tetrazole or CONR$_{13}$R$_{14}$ (wherein R$_{13}$ and R$_{14}$ are independently H or C$_1$ to C$_6$ hydrocarbyl)

Z$_1$ and Z$_2$ (which may be the same or different) are optional and each represents one or more substituents in the aromatic ring system, such substituents being independently selected from C$_1$ to C$_6$ alkyl (two such alkyl substituents optionally forming a ring fused to one or both of the aromatic rings), C$_1$ to C$_6$ alkoxy, C$_1$ to C$_6$ thioalkoxy, carboxy, C$_1$ to C$_6$ carboalkoxy, nitro, trihalomethyl, hydroxy, —NR$_{15}$R$_{16}$ (wherein R$_{15}$ and R$_{16}$ are independently H or C$_1$ to C$_6$ alkyl), C$_1$ to C$_6$ alkylaryl, C$_1$ to C$_6$ alkyl(substituted aryl), halo, sulphonamide and cyano and D is —O—R$_{17}$—Q or

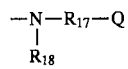

(wherein Q is H or a carbocyclic or heterocyclic group which may optionally be substituted; $R_{17}$ is absent or is $C_1$ to $C_{10}$ hydrocarbylene, optionally substituted by —OH, —SH, halogen, —$CO_2R_{19}$ or —$CONR_{19}R_{20}$ (wherein $R_{19}$ and $R_{20}$ are independently H or $C_1$ to $C_6$ hydrocarbyl), and optionally having up to three carbon atoms replaced by —O—, —S— or —$NR_{21}$— (wherein $R_{21}$ is H or an N-blocking group), provided that $R_{17}$ contains at least one carbon atom if Q is H and that $R_{17}$ does not contain —O—O—; and $R_{18}$ is H or $C_1$ to $C_6$ alkyl or forms an alkylene (e.g. $C_1$ to $C_4$ alkylene link to Q)
and pharmaceutically acceptable salts thereof.

The compounds of the invention are found to display either antagonist or partial agonist activity at gastrin and/or cholecystokinin receptors. Certain preferred compounds are potent cholecystokinin antagonists, but display comparatively little antagonist activity at the gastrin receptor.

The terms "hydrocarbyl" and "hydrocarbylene", as used herein, refer respectively to monovalent and divalent groups consisting of carbon and hydrogen. Hydrocarbyl groups thus include alkyl, alkenyl, alkynyl, cycloalkyl, cycloalkenyl, aryl, alkylaryl, alkenylaryl, alkynylaryl, cycloalkylaryl, and cycloalkenylaryl groups, in both straight and branched chain forms.

A "carbocyclic" group, as the term is used herein, comprises one or more closed chains or rings, which consist entirely of carbon atoms. Included in such groups are alicyclic groups such as cyclopropyl, cyclobutyl, cyclopentyl, cyclohexyl and adamantyl, as well as aromatic groups such as phenyl, naphthyl, indanyl, fluorenyl, (1,2,3,4)-tetrahydronaphthyl, indenyl and isoindenyl.

The term "aryl" is used herein to refer to aromatic carbocyclic groups, including those mentioned above. When reference is made herein to "substituted aryl", the substituents are preferably from 1 to 3 in number (and more usually 1 or 2 in number), and are preferably independently selected from $C_1$ to $C_6$ alkyl, $C_1$ to $C_6$ alkoxy, $C_1$ to $C_6$ thioalkoxy, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulphonamide and cyano.

A "heterocyclic" group comprises one or more closed chains or rings which have at least one atom other than carbon in the closed chain or ring. Examples include thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinal, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl.

The term "halogen", as used herein, refers to any of fluorine, chlorine, bromine and iodine. Most usually, however, halogen substituents in the compounds of the invention are chlorine or fluorine substituents.

$R_{11}$ (or $R_{11}$ together with $R_{12}$) may be any of a wide range of pharmaceutically acceptable N-blocking groups. Generally, $R_{11}$ will be a group of the formula $R_{22}$—$X_1$—(—N($R_{23}$)—$R_{24}$—$X_2$)$_r$—, wherein $X_1$ and $X_2$ are independently —C(O)—, —O—C(O)—, —SO—, or —$SO_2$—

$R_{22}$ is $C_1$ to $C_{20}$ hydrocarbyl, optionally substituted by $C_1$ to $C_6$ alkoxy, $C_1$ to $C_6$ thioalkoxy, halo, nitro, or tri($C_1$ to $C_3$ alkyl)silyl, $R_{23}$ is H or is linked to $R_{22}$ (e.g. by a —C(O)— group)

$R_{24}$ is $C_1$ to $C_3$ hydrocarbylene, and r is 0 or 1.

$R_{22}$ is preferably selected from $C_1$ to $C_6$ straight or branched chain alkyl or haloalkyl, alkenyl, phenyl, benzyl, fluorenyl, 1-adamantyl, 2-adamantyl, 4-toluenyl, biphenylisopropyl, 2-nitrophenyl, 2-trimethylsilylethyl and 4-methoxybenzyl. Particularly preferred structures for $R_{22}$—$X_1$— are t-butylacetyl, t-butyloxycarbonyl, phenyloxycarbonyl, benzyloxycarbonyl, 1-adamantyloxycarbonyl, 2-adamantyloxycarbonyl, fluorenyloxycarbonyl, 4-toluenesulphonyl, biphenylisopropoxycarbonyl, 2-nitrophenylsulphenyl, 2-trimethylsilylethyloxycarbonyl and 4-methoxybenzyloxycarbonyl.

When $R_{23}$ is a —C(O)— group linked to $R_{22}$, $R_{22}$—$X_1$—N($R_{23}$)— may form a group such as phthaloyl or maleoyl.

$R_{24}$ is preferably $C_1$ to $C_3$ alkylene or $C_1$ to $C_3$ alkenylene, and is most preferably —$(CH_2)_2$—. $X_1$ and $X_2$ (when present) are most usually —O—C(O)— and —C(O)— respectively.

Alternatively, as indicated above, $R_{11}$ and $R_{12}$ may together form an N-blocking group. For example, $R_{12}$ may be —C(O)-linked to $R_{11}$, such that $R_{11}$—N($R_{12}$)— constitutes a group such as phthaloyl or maleoyl.

$R_8$ is preferably absent or is $C_1$ to $C_3$ alkylene, while $R_9$ and $R_{10}$ are preferably $C_1$ to $C_3$ alkylene, e.g. methylene.

Preferably, Q is selected from phenyl, naphthyl, indanyl, fluorenyl, (1,2,3,4)-tetrahydronaphthyl, indenyl, pyridyl, isoindenyl, cycloalkyl and adamantyl, and derivatives thereof having one or more substituents (e.g. up to three) selected from $C_1$ to $C_6$ alkyl, $C_1$ to $C_6$ alkoxy, $C_1$ to $C_6$ thioalkoxy, carboxy, $C_1$ to $C_6$ carboalkoxy, nitro, trihalomethyl, hydroxy, —$NR_{25}R_{26}$ (wherein $R_{25}$ and $R_{26}$ are independently H or $C_1$ to $C_6$ alkyl), aryl, substituted aryl, $C_1$ to $C_6$ alkylaryl, $C_1$ to $C_6$ alkyl(substituted aryl), halo, sulphonamide and cyano.

$R_{17}$, when present, may be aromatic or non-aromatic. In a particular group of compounds according to the invention, $R_{17}$ is $C_1$ to $C_6$ (e.g. $C_1$ to $C_3$) hydrocarbylene, which may have from 1 to 3 substituents selected from —OH, —SH, halogen, —$CO_2R_{19}$ and —$CONR_{19}R_{20}$ (wherein $R_{19}$ and $R_{20}$ are independently H or $C_1$ to $C_6$ alkyl). In a further particular sub-group, $R_{17}$ is $C_1$ to $C_6$ (e.g. $C_1$ to $C_6$) alkylene, especially straight-chain alkylene, and is unsubstituted.

Preferably, D is

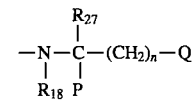

$R_{18}$ is H or methyl, $R_{27}$ is H or methyl, or is an alkylene chain linked to Q, n is from 0 to 3, and P is —H, —$CH_2OH$, —$CO_2R_{19}$ or —$CONR_{19}R_{20}$ (wherein $R_{19}$ and $R_{20}$ are independently H or $C_1$ to $C_6$ alkyl).

$R_{21}$ is preferably H or $C_1$ to $C_{20}$ hydrocarbyl, $C_1$ to $C_{20}$ hydrocarbylcarbonyl or $C_1$ to $C_{20}$ hydrocarbyloxycarbonyl, and more preferably H, $C_1$ to $C_6$ alkyl, $C_1$ to $C_6$ alkylcarbonyl, $C_1$ to $C_6$ alkyloxycarbonyl, aryl, aryl($C_1$ to $C_6$ alkyl), aryl(C$_1$ to C$_6$ alkylcarbonyl) or aryl(C$_1$ to C$_6$ alkyloxycarbonyl).

The carbon atoms to which R$_2$, R$_4$, and R$_6$ are attached in formula I above are asymmetric. When P is present, and is other than hydrogen, the carbon atom to which it is attached is also asymmetric. Such carbon atoms may all be in either configuration, but it is preferred that those to which R$_2$, R$_4$ and R$_{27}$ are attached are in the L configuration.

Pharmaceutically acceptable salts of the acidic compounds of the invention include salts with alkali metals and alkaline earth metals, such as sodium, potassium, calcium and magnesium, and salts with organic bases. Suitable organic bases include amines such as N-methyl-D-glucamine.

Pharmaceutically acceptable salts of the basic compounds of the invention include salts derived from organic or inorganic acids. Suitable acids include hydrochloric acid, phosphoric acid, oxalic acid, maleic acid, succinic acid and citric acid.

The compounds of the invention may be prepared by coupling the constituent amino acid moieties by conventional methods. Such methods are described in detail in "The Peptides, Vol. 1", Gross and Meinenhofer, Eds., Academic Press, N.Y., 1979. In these methods, the amide bonds between adjacent amino acid moieties are formed by coupling the free carboxylic acid group of one amino acid moiety with the free nitrogen atom of the second amino acid moiety.

Suitable coupling methods include the carbodiimide method (using, for example, 1,3-dicyclohexylcarbodiimide [DCCI] or 1-(3-dimethylaminopropyl)-3-ethylcarbodiimide-dehydrochloride [EDCI], and optionally an additive such as 1-hydroxybenzotriazole [HOBT] to prevent racemization), the azide method, the mixed anhydride method, the symmetrical anhydride method, the acid chloride method, the use of bis (2-oxo-3-oxazolidinyl) phosphinic chloride [BOP-Cl], and the active ester method (using, for example, N-hydroxysuccinimide esters, 4-nitrophenyl esters or 2,4,5-trichlorophenol esters).

The coupling reactions are generally conducted under an inert atmosphere, such as an atmosphere of nitrogen or argon. Suitable solvents for the reactants include methylene chloride, tetrahydrofuran [THF], dimethoxyethane [DME] and dimethylformamide [DMF].

Carboxylic and amino groups other than those which it is desired to couple by means of the coupling reaction are first protected by protecting groups. Suitable groups for protecting amino groups include benzyloxycarbonyl [Cbz], t-butyloxycarbonyl [Boc], 2,2,2-trichloroethoxycarbonyl [Troc], t-amyloxycarbonyl, 4-methoxybenzyloxycarbonyl, 2-(trichlorosilyl)ethoxycarbonyl, 9-fluorenylmethoxycarbonyl [FMOC], phthaloyl, acetyl, formyl and trifluoroacetyl (see, for example, "The Peptides, Vol. 3", Gross and Meinenhofer, Eds., Academic Press, N.Y., 1981). Suitable groups for protecting carboxylic groups include esters such as methyl, ethyl, t-butyl, 2,2,2-trichloroethyl, benzyl, 4-nitrobenzyl and allyl.

After the coupling reaction, protecting groups may be removed, if desired, by methods well known in the art, such as by acid or base catalysed hydrolysis or hydrogenolysis.

The compounds of the invention in which one or more of R$_3$, R$_5$ and R$_7$ is a methyl group may be prepared by the above described methods using appropriately N-methylated amino acids. Such N-methyl amino acids may themselves be prepared by the methods of Benoiton (Can. J. Chem., 55, 906, (1977)), Shuman ("Peptides: Proceedings of the 7th American Symposium", Rich and Gross, Eds., Pierce Chemical Co., 1981, p.617) or Freidinger (J. Org. Chem., 48, 77, (1983)).

Appropriate routes for the synthesis of unnatural or α-methylated chiral amino acid starting materials are described in "Synthesis of Optically Active α-Amino Acids", by Williams, R. M., Pergamon Press, Oxford, 1989.

Those compounds in which one or more of B$_1$, B$_2$ and B$_3$ is —CH$_2$— may be prepared by methods which are analogous to those described by Martinez (J. Med. Chem., 30, 1366 (1987)). The appropriately protected amino acid is reduced to the corresponding aldehyde, which is then allowed to condense with the free amino group of the second amino acid. The resulting Schiff base is then reduced using sodium cyanoborohydride to yield the desired compound.

The invention thus provides a method of preparing a compound of formula I above, said method comprising the step of coupling a suitably protected compound of the formula

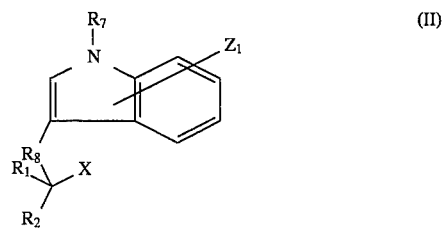
(II)

with a suitably protected compound of the formula

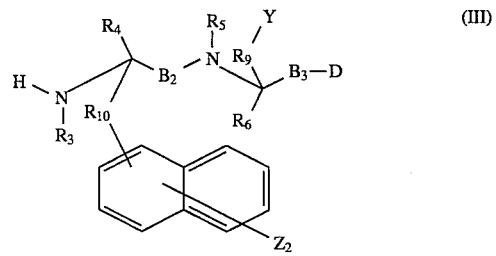
(III)

wherein R$_1$, R$_2$, R$_3$, R$_4$, R$_5$, R$_6$, R$_7$, R$_8$, R$_9$, R$_{10}$, Z$_1$, Z$_2$, Y, D, B$_2$ and B$_3$ are as defined above, and X is —COOH or —CHO, said method comprising the further step of reducing the resulting Schiff base when X is —CHO.

The compound of formula III is preferably prepared by coupling a suitably protected compound of the formula

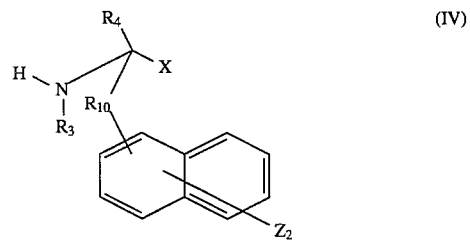
(IV)

with a suitably protected compound of the formula

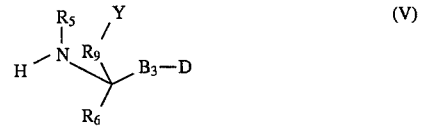
(V)

When D is —N(R$_{18}$)R$_{17}$—Q, the compound of formula V may in turn may be prepared by coupling a suitably protected compound of the formula

wherein X is —COOH or —CHO, with a suitably protected compound of the formula H-D, said method comprising the further step of reducing the resulting Schiff base when X is —CHO.

Alternatively, when D is —O—$R_{17}$—Q, the compound of formula V may be prepared by coupling a suitably protected compound of the formula VI above, wherein X is —COO⁻, with a suitably protected compound of the formula Br—$R_{17}$—Q.

The invention also provides a method of preparing a compound of formula I above, said method comprising the step of coupling a suitably protected compound of the formula

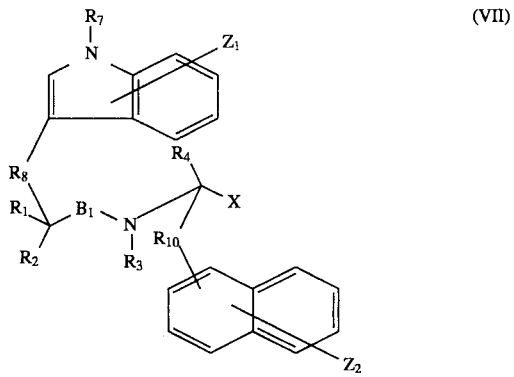

with a suitably protected compound of formula V above, wherein $R_1$, $R_2$, $R_3$, $R_4$, $R_5$, $R_6$, $R_7$, $R_8$, $R_9$, $R_{10}$, $Z_1$, $Z_2$, Y, D, $B_1$ and $B_3$ are as defined above, and X is —COOH or —CHO, said method comprising the further step of reducing the resulting Schiff base when X is —CHO.

The compounds of formula VII above may be prepared by coupling a suitably protected compound of formula II with a suitably protected compound of formula IV.

The invention further provides a method of preparing a compound of formula I above, said method comprising the step of coupling a suitably protected compound of the formula

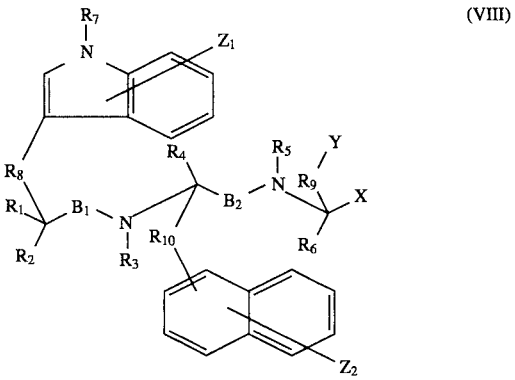

wherein $R_1$, $R_2$, $R_3$, $R_4$, $R_5$, $R_6$, $R_7$, $R_8$, $R_9$, $R_{10}$, $Z_1$, $Z_2$, Y, $B_1$ and $B_2$ are as defined above and X is —COOH or —CHO, with a suitably protected compound of the formula H-D, wherein D is as defined above, said method comprising the further step of reducing the resulting Schiff base when X is —CHO.

Compounds of formula VIII above may of course be prepared by coupling a suitably protected compound of formula VII above with a suitably protected compound of formula VI.

In a still further aspect, the invention provides a method of preparing a compound of formula I above, said method comprising the step of coupling a suitably protected compound of formula VIII above, wherein $R_1$, $R_2$, $R_3$, $R_4$, $R_5$, $R_6$, $R_7$, $R_8$, $R_9$, $R_{10}$, $Z_1$, $Z_2$, Y, $B_1$ and $B_2$ are as defined above and X is —COO⁻, with a suitably protected compound of the formula Br—$R_{17}$—Q, wherein $R_{17}$ and Q are as defined above.

Pharmaceutically acceptable salts of the acidic or basic compounds of the invention can of course be made by conventional procedures, such as by reacting the free base or acid with at least a stoichiometric amount of the desired salt-forming acid or base.

The compounds of the invention can be administered by oral or parenteral routes, including intravenous, intramuscular, intraperitoneal, subcutaneous, rectal and topical administration.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride.

Aqueous suspensions according to the invention may include suspending agents such as cellulose derivatives, sodium alginate, polyvinyl-pyrrolidone and gum tragacanth, and a wetting agent such as lecithin.

Suitable preservatives for aqueous suspensions include ethyl and n-propyl p-hydroxybenzoate.

The invention is now further illustrated by means of the following Examples.

EXAMPLE 1

Preparation of
N-t-Butyloxycarbonyl-L-tryptophyl-L-3-(2-naphthyl) alanyl-L-aspartyl-L-phenylalaninamide a. N-t-Butyloxycarbonyl-L-tryptophyl-L-3-(2-naphthyl)alanine A suspension of L-3-(2-naphthyl)alanine (0.43 g, 2.0 mmol) and sodium hydrogencarbonate (0.34 g, 4.0 mmol) in water (6 ml) was treated with a suspension of N-t-butyloxycarbonyl-L-tryptophan N-hydroxysuccinimide ester (0.8 g, 2.0 mmol) in ethanol (10 ml). The mixture was stirred at room temperature for 24 hrs. The ethanol was evaporated in vacuo, the residue was diluted with water (20 ml) and acidified to pH 2 with 1N hydrochloric acid. The product was extracted with ethyl acetate (2×20 ml). The organic phase was dried (MgSO$_4$) and evaporated in vacuo to afford a colourless oil. Yield: 1.00 g 100%

The crude product was used for the preparation of the N-hydroxysuccinimide ester.

$^1$H NMR (DMSO-d$_6$) δ12.8 (1H, br,s), 10.8 (1H,s), 8.1 (1H,d), 7.8 (3H,m), 7.7 (1H,s), 7.5 (4H,m), 7.0 (4H,m), 6.7 (1H,d), 4.6 (1H,m), 4.1 (1H,m), 2.7–3.5 (4H,m), 1.2 (9H,s).

b. N-t-Butyloxycarbonyl-L-tryptophyl-L-3-(2-naphthyl)alanine N-hydroxysuccinimide ester A solution of N-t-butyloxycarbonyl-L-tryptophyl-L-3-(2-naphthyl)alanine (0.50 g, 1.0 mmol) and N-hydroxysuccinimide (0.12 g, 1.0 mmol) in dry 1,2-dimethoxyethane (5 ml) was cooled in an ice-water bath. Dicyclohexylcarbodiimide (0.22 g, 1.0 mmol) was added. The mixture was stirred at 5° overnight. The precipitated N,N-dicyclohexylurea was removed by filtration and the solvent was evaporated in vacuo to afford a colourless oil (0.63 g). The crude product was used for the coupling.

$^1$H NMR (DMSO-d$_6$) δ10.7 (1H, s), 8.8 (1H, d), 7.8 (4H, m), 7.5 (4H, m), 7.3 (1H, m), 7.0 (3H, m), 6.7 (1H, d), 5.1 (1H, m), 4.2 (1H, m), 2.8 (4H, s), 2.6–3.3 (4H, m) and 1.2 (9H, s).

c. N-t-Butyloxycarbonyl-β-O-benzyl-L-aspartyl-L-phenylalaninamide

A solution of L-phenylalaninamide hydrochloride (1.00 g, 5.0 mmol) and sodium hydrogencarbonate (0.42 g, 5.0 mmol) in water (10 ml) was treated with a solution of N-t-butyloxycarbonyl-β-O-benzyl-L-aspartic acid N'-hydroxysuccinimide ester (2.10 g, 5.0 mmol) in 1,2-dimethoxyethane (15 ml). After stirring overnight at room temperature, water (10 ml) was added and the mixture was acidified to pH 2 with 1N hydrochloric acid. The suspension was cooled in an ice-water bath for 2 hrs, the precipitate was filtered, washed with cold water, dried in vacuo at room temperature.

Yield: 2.07 g, 89%, m.p 135° C., [α]$_D$=−9.3° (c=0.9, DMSO), $^1$H NMR (DMSO-d$_6$) δ7.7 (1H, d), 7.3 (5H, m), 7.2 (7H, m), 4.4 (1H, m), 4.3 (1H, m), 3.0 (1H, m), 2.8 (1H, m), 2.7 (1H, m), 2.5 (1H, m), and 1.3 (9H, s).

d. N-t-Butyloxycarbonyl-L-tryptophyl-L-3-(2-naphthyl)alanyl-β-O-benzyl-L-aspartyl-L-phenylalaninamide N-t-butyloxycarbonyl-β-O-benzyl-L-aspartyl-L-phenylalaninamide (0.47 g, 1.0 mmol) was dissolved in trifluoroacetic acid (3 ml) and the solution was kept at room temperature for 1 hr. The trifluoroacetic acid was removed in vacuo, the residue was dissolved in dry 1,2-dimethoxyethane (6 ml), triethylamine (0.5 ml, 4.0 mmol) and N-t-butyloxycarbonyl-L-tryptophyl-L-3-(2-naphthyl)alanine N-hydroxysuccinimide ester (0.6 g, 1.0 mmol) dissolved in 1,2-dimethoxyethane (4 ml) were added. The mixture was stirred at room temperature overnight, then cooled in an ice-water bath and diluted with cold water (10 ml). The stirring was continued for 1 hr, the solid was filtered, washed with cold water and dried in vacuo at room temperature. Yield: 0.72 g, 84%

The crude product was recrystallized from aqueous ethanol to afford colourless crystals (0.56 g, 65%), m.p.:175°–180° C., [α]$_D$=−18.5° (c=1, DMSO), found: C,69.13; H, 6.16; N,9.99. C$_{49}$H$_{52}$N$_6$O$_8$ requires C,69.0; H, 6.14; N,9.85%. $^1$H NMR (DMSO-d$_6$) δ10.7 (1H, s), 8.5 (1H, d), 8.0 (2H, m), 7.8 (4H, m), 6.8–7.5 (20H, m), 5.0 (2H, s), 4.6 (2H, m), 4.4 (1H, m), 4.1 (1H, m), 2.5–3.2 (8H, m), 1.2 (9H, s)

e. N-t-Butyloxycarbonyl-L-tryptophyl-L-3-(2-naphthyl)alanyl-L-aspartyl-L-phenylalaninamide N-t-Butyloxycarbonyl-L-tryptophyl-β-O-benzyl-L-aspartyl-L-phenylalaninamide (0.3 5 g, 0.4 mmol) was suspended in methanol (40 ml), acetic acid (0.5 ml) and 10% palladium on activated carbon catalyst (0.035 g) were added. The air was displaced by a slow stream of nitrogen, then hydrogen. The catalyst was kept in suspension by vigorous stirring. The mixture was kept under hydrogen overnight. The catalyst was filtered, washed with hot methanol (20 ml), the filtrate was evaporated under reduced pressure. Yield: 0.28 g, 90%

The product was recrystallized from aqueous ethanol to afford colourless crystals (0.17 g, 64%), m.p.: 230°–232°, [α]$_D$–21° (c=1.0, DMSO), found C,62.02; H,6.37; N,10.21%. C$_{42}$H$_{46}$N$_6$O$_8$ x 1 mol EtOH x 2.8 mol H$_2$O requires C, 61.97; H, 6.43; N,10.27%. $^1$H NMR (DMSO-d$_6$) δ10.7 (1H, s), 8.5 (1H, d), 8.0 (2H, m), 7.7 (4H, m), 6.9–7.5 (15H, m), 6.8 (1H, d), 4.7 (1H,m), 4.5(1H, m), 4.4 (1H, m), 4.1 (1H, m), 2.6–3.2 (8H, m), 1.2 (9H, s).

EXAMPLE 2

Preparation of N-t-Butyloxycarbonyl-L-tryptophyl-L-3-(2-naphthyl)alanyl-L-aspartylphenethylamide The compound was prepared as in example 1 except that N-t-butyloxycarbonyl-β-O-benzyl-L-aspartylphenethylamide (prepared by coupling N-t-butyloxycarbonyl-β-O-benzyl-L-aspartic acid N'-hydroxysuccinimide ester with phenethylamine in DME) was used instead of N-t-butyloxycarbonyl-β-O-benzyl-L-aspartyl-L-phenylalaninamide in step d.

The product was a solid m.p. 140°–3°, [α]$_D$ −8.9° (c=0.9 in DMSO), $^1$H NMR(DMSO-d$_6$) δ10.9 (1H, s), 8.4 (1H, m), 8.1 (2H, m), 6.8–7.9 (17H, m), 6.7 (1H, m), 4.6 (1H, m), 4.5 (1H, m), 4.1 (1H, m), 2.3–3.5 (10H, m), 1.2 (9H,s).

EXAMPLE 3

Preparation of N-t-Butyloxycarbonyl-L-tryptophyl-D-3-(2-naphthyl)alanyl-L-aspartyl-L-phenylalaninamide The compound was prepared as in example 1 except that D-3-(2-naphthyl)alanine was used in step a instead of the L-isomer. M.p. 184°–6° [α]$_D$ −28.0° (c=0.5 in DMF), Found C, 65.75; H, 5.87; N, 10.88% C$_{42}$H$_{46}$N$_6$O$_8$ requires C, 66.13; H, 5.87; N, 11.02% $^1$H NMR (DMSO-d$_6$)δ10.7 (1H, s), 8.5 (1H, d), 8.0 (2H, m), 7.7 (4H, m), 6.9–7.5 (15H, m), 6.8 (1H, d), 4.7 (1H, m), 4.5 (1H, m), 4.4 (1H, m), 4.1 (1H, m), 2.6–3.2 (8H, m), 1.2 (9H, s).

EXAMPLE 4

Preparation of N-t-Butyloxycarbonyl-L-tryptophyl-L-3-(1-naphthyl)alanyl-L-aspartyl-L-phenylalaninamide The compound was prepared as in example 1 except that L-3-(1-naphthyl)alanine was used in step a instead of the 2-isomer. M.p. 240°–2°, [α]$_D$ −42.0° (c=0.5 in DMF), Found C, 66.09; H, 6.06; N, 10.93% C$_{42}$H$_{46}$N$_6$O$_8$ requires C, 66.13; H, 5.87; N, 11.02% $^1$H NMR (DMSO-d$_6$) δ10.7 (1H, s), 8.4 (1H, d), 8.2 (1H, d), 8.0 (1H, d), 7.9 (1H, d), 7.9 (1H, d), 7.7 (1H, m), 7.5 (3H, m), 7.3 (4H, m), 7.2 (5H, m), 7.0 (5H, m), 6.7 (1H, d), 4.7 (1H, m), 4.5 (1H, m), 4.4 (1H, m), 4.0 (1H, m), 3.6-2.4 (8H, m) and 1.2 (9H, s3).

EXAMPLE 5

Preparation of
N-t-Butyloxycarbonyl-L-tryptophyl-L-3-(2-naphthyl)
alanyl-L-aspartyl-L-phenylalanyl-(N-methyl)amide This was prepared as in example 1 but using t-butyloxycarbonyl-β-O-benzyl-L-aspartyl-L-phenylalanyl-(N-methylamide) (prepared by coupling N-t-butyloxycarbonyl-β-O-benzyl-L-aspartic acid N'-hydroxysuccinimide ester with L-phenylalanyl-(N-methyl)amide in DME) instead of t-butyloxycarbonyl-β-O-benzyl-L-aspartyl-L-phenylalaninamide in step d. M.p. 227°–232° dec., $[\alpha]_D$ –70.0° (c=0.21 in ethanol), found: C, 66.42; H, 6.16; N, 10.64. $C_{43}H_{47}N_6O_8$ requires C, 66.57; H, 6.11; N, 10.83%, $^1$H NMR (DMSO-$d_6$) δ 10.8 (1H, s), 8.4 (1H, d), 8.0 (2H, m), 7.7 (4H, m), 7.4 (4H, m), 7.2 (7H, m), 6.9 (4H, m), 4.6 (1H, m), 4.5 (1H, m), 4.3 (1H, m), 4.0 (1H, m), 2.9 (8H, m), 2.5 (3H, d) and 1.2 (9H, s).

EXAMPLE 6

Preparation of
N-t-Butyloxycarbonyl-L-tryptophyl-L-3-(2-naphthyl)
alanyl-L-aspartyl-L-phenylalanyl-(N,Ndimethyl)amide This was prepared as in example 1 but using t-butyloxycarbonyl-β-O-benzyl-L-aspartyl-L-phenylalanyl-(N,N-dimethylamide) (prepared by coupling N-t-butyloxycarbonyl-β-O-benzyl-L-aspartic acid N'-hydroxysuccinimide ester with L-phenylalanyl-(N,N-dimethylamide) in DME) instead of t-butyloxycarbonyl-β-O-benzyl-L-aspartyl-L-phenylalaninamide in step d. The compound was a gum, $[\alpha]_D$ –37.7° (C=0.37 in ethanol), found: C, 63.19; H, 6.51; N, 10.33. $C_{44}H_{45}N_6O_8$·2.5 $H_2O$ requires C, 63.22; H, 6.63; N, 10.05%, $^1$H NMR (DMSO-$d_6$) δ10.7 (1H, s), 8.4 (1H, d), 8.0 (1H, d), 7.9 (1H, d), 7.7 (4H, m), 7.4 (3H, m), 7.2 (7H, m), 6.9 (4H, m), 4.8 (1H, m), 4.6 (1H, m), 4.5 (1H, m), 4.1 (1H, m), 3.0 (6H, m), 2.7 (6H, d), 2.6 (2H, m) and 1.2 (9H, s).

EXAMPLE 7

Preparation of
N-t-Butyloxycarbonyl-L-tryptophyl-L-3-(2-naphthyl)
alanyl-L-aspartyl-L-(4-methoxyphenylalanin)amide This was prepared as in example 1 but using t-butyloxycarbonyl-β-O-benzyl-L-aspartyl-L-4-methoxyphenylalaninamide (prepared by coupling N-t-butyloxycarbonyl-β-O-benzyl-L-aspartic acid N'-hydroxysuccinimide ester with L-4-methoxyphenylalaninamide in DME) instead of t-butyloxycarbonyl-β-O-benzyl-L-aspartyl-L-phenylalaninamide in step d. M.p. 182° $[\alpha]_D$ –45.7° (c=0.33 in ethanol), found: C, 63.59; H, 6.23; N, 10.28. $C_{43}H_{48}N_6O_9$·$H_2O$ requires C, 63.69; H, 6.22; N, 10.36%, $^1$H NMR (DMSO-$d_6$) δ10.7 (1H, s), 8.5 (1H, d), 7.9 (2H, m), 7.8 (4H, m), 7.4 (6H, m), 7.0 (6H, m), 6.8 (3H, m), 4.6 (1H, m), 4.5 (1H, m), 4.3 (1H, m), 4.1 (1H, m), 3.5 (3H, s), 2.8 (8H, m), and 1.2 (9H, s).

EXAMPLE 8

Preparation of
N-t-Butyloxycarbonyl-L-tryptophyl-L-3-(2-naphthyl)
alanyl-L-aspartyl-(4-chlorophenethyl)amide This was prepared as in example 1 but using t-butyloxycarbonyl-β-O-benzyl-L-aspartyl-4-chlorophenethyl-amide (prepared by coupling N-t-butyloxycarbonyl-β-O-benzyl-L-aspartic acid N'-hydroxysuccinimide ester with 4-chlorophenethylamine in DME) instead of t-butyloxycarbonyl-β-O-benzyl-L-aspartyl-L-phenylalaninamide in step d. M.p. 175°–80°, found: C, 65.12; H, 5.66; N, 9.31. $C_{41}H_{44}N_5O_7Cl$ requires C, 65.29; H, 5.88; N, 9.29%, $^1$H NMR (DMSO-$d_6$) δ10.7 (1H, s), 8.4 (1H, d), 8.0 (1H, d), 7.8 (5H, m), 7.3 (7H, m), 7.2 (2H, m) 7.0 (2H, m), 6.9 (2H, m), 4.6 (1H, m), 4.5 (1H, m), 4.3 (1H, m), 4.1 (1H, m), 3.5 (3H, s), 2.8 (8H, m), and 1.2 (9H, s).

EXAMPLE 9

Preparation of
N-t-Butyloxycarbonyl-L-tryptophyl-L-3-(2-naphthyl)
alanyl-L-aspartyl-L-phenylalaninol This was prepared as in example 1 but using t-butyloxycarbonyl-β-O-benzyl-L-aspartyl-L-phenylalaninol (prepared by coupling N-t-butyloxycarbonyl-β-O-benzyl-L-aspartic acid N'-hydroxysuccinimide ester with L-phenylalaninol in DME) instead of t-butyloxycarbonyl-β-O-benzyl-L-aspartyl-L-phenylalaninamide in step d. M.p. 171°–76°, $[\alpha]_D$ –60.0° (c=0.2 in ethanol) found: C, 67.43; H, 6.47; N, 9.53. $C_{42}H_{47}N_5O_8$ requires C, 67.27; H, 6.32; N, 9.34%, $^1$H NMR (DMSO-$d_6$) 10.7 (1H, s), 8.4 (1H, d), 7.9 (1H, d), 7.7 (5H, m), 7.2 (10H, m), 7.0 (2H, m), 6.9 (2H, m), 4.6 (1H, m), 4.5 (1H, m), 4.1 (1H, m), 3.8 (1H, m) 3.2 (2H, m), 2.8 (8H, m) and 1.2 (9H, s).

EXAMPLE 10

Preparation of
N-t-Butyloxycarbonyl-L-tryptophyl-L-3-(2-naphthyl)
alanyl-L-aspartyl-(4-methoxy)phenethylamide This was prepared as in example 1 but using t-butyloxycarbonyl-β-O-benzyl-L-aspartyl-4-methoxyphenethylamide (prepared by coupling N-t-butyloxycarbonyl-β-O-benzyl-L-aspartic acid N'-hydroxysuccinimide ester with 4-methoxyphenethylamine in DME) instead of t-butyloxycarbonyl-β-O-benzyl-L-aspartyl-L-phenylalaninamide in step d. M.p. 144°–7°, $[\alpha]_D$ –30.6° (c=0.46 in ethanol), found: C, 66.38; H, 6.61; N, 9.27. $C_{42}H_{47}N_5O_8$·0.5 $H_2O$ requires C, 66.41; H, 6.37; N, 9.22%, $^1$H NMR (DMSO-$d_6$) δ10.8 (1H, s), 8.4 (1H, d), 8.0 (1H, d), 7.7 (5H, m), 7.4 (5H, m), 7.0 (4H, m), 6.9 (2H, m), 6.8 (2H, m), 4.6 (1H,5 m), 4.4 (1H, m), 4.1 (1H, m), 3.6 (3H, s) 3.1 (2H, m), 2.8 (6H, m), 2.6 (2H, m) and 1.2 (9H, s).

EXAMPLE 11

Preparation of
N-t-Butyloxycarbonyl-L-tryptophyl-L-3-(2-naphthyl)
alanyl-L-aspartyl-L-(4-chlorophenylalanin)amide This was prepared as in example 1 but using t-butyloxycarbonyl-β-O-benzyl-L-aspartyl-L-4-chlorophenylalaninamide (prepared by coupling N-t-butyloxycarbonyl-β-O-benzyl-L-aspartic acid N'-hydroxysuccinimide ester with L-4-chlorophenylalaninamide in DME) instead of t-butyloxycarbonyl-β-benzyl-L-aspartyl-L-phenylalaninamide in step d. M.p. >230°, $[\alpha]_D$ –7.8° (c=0.13 in DMF), found: C, 63.39; H, 5.70; N, 10.51. $C_{42}H_{45}N_6O_8Cl$ requires C, 63.27; H, 5.69; N, 10.54%, $^1$H NMR (DMSO-$d_6$) δ10.7 (1H, s), 8.4 (1H, d), 7.9 (2H, m), 7.7 (4H, m), 7.3 (10H, m), 6.9 (4H, m), 6.9 (1H, m), 4.6 (1H, m), 4.5 (1H, m), 4.4 (1H, m), 4.0 (1H, m), 2.8 (8H, m), and 1.2 (9H, s).

EXAMPLE 12

Preparation of
N-t-Butyloxycarbonyl-L-tryptophyl-L-3-(2-naphthyl)
alanyl-D-aspartyl-L-phenylalaninamide a. N-t-Butyloxycarbonyl-β-O-benzyl-D-aspartyl-L-phenylalaninamide N-t-butyloxycarbonyl-β-O-benzyl-D-aspartic acid (602 mg, 1.86 mmol) was dissolved in 1,2-dimethoxyethane (5 ml). N-hydroxysuccinimide (215 mg, 1.86mmol) was added followed by dicyclohexylcarbodiimide (385 mg, 1.86mmol). After stirring overnight at room temperature the solution was filtered and the filtrate added to a solution of L-phenylalaninamide (336 mg, 2.05 mmol) in 1,2-dimethoxyethane (10 ml). The solution was stirred overnight at room temperature and diluted with water (50 ml). The mixture was acidified to pH 2 with 1N hydrochloric acid. The suspension was extracted with ethyl acetate (2×30 ml) and the organic layer washed with water. The organic layer was dried filtered and evaporated to leave a white foam. Yield: 910 mg, $^1$H NMR (CDCl$_3$) δ7.2–7.4 (10H, m), 6.9 (1H, d), 6.4 (1H, s), 5.5 (1H, s), 5.1 (2H, s), 4.7 (1H, m), 4.5 (1H, m), 2.6–3.3 (4H, m), 1.4 (9H, s).

b. N-t-Butyloxycarbonyl-D-aspartyl-L-phenylalaninamide

N-t-Butyloxycarbonyl-β-O-benzyl-D-aspartyl-L-phenylalaninamide (0.50 g, 1.06 mmol) was dissolved in methanol and 10% palladium on charcoal was added. The reaction mixture was stirred under an atmosphere of hydrogen for four hours. The reaction mixture was filtered through celite and the filtrate evaporated to leave a white solid 382 mg, $^1$H NMR (DMSO-d$_6$) δ8.0 (1H d ), 7.0–7.4 (8 H, m ), 4.4 (1H, m), 4.2 (1H, m), 2.3–3.1 (4H, m), 1.4 (9H, s).

c. N-t-Butyloxycarbonyl-L-tryptophyl-L-3-(2-naphthyl)alanyl-D-aspartyl-L-phenylalaninamide N-t-Butyloxycarbonyl-D-aspartyl-L-phenylalaninamide (0.38 g, 0.43 mmol) was stirred with trifluoroacetic acid (5 ml) for 16 h. The solution was evaporated to dryness and the residue triturated with ether to leave the TFA salt of D-aspartyl-L-phenylalaninamide which was filtered off and dried under vacuum. The salt (283 mg, 0.72 mmol) was dissolved in dry dimethylformamide (5 ml) and triethylamine (0.2 ml) was added followed by N-t-butyloxycarbonyl-L-tryptophyl-L-3-(2-naphthyl)alanine N-hydroxysuccinimide ester (Example 1 step b., 420 mg, 0.72 mmol). The solution was stirred for 48 h and poured onto ice cool water (50 ml). The white precipitate formed was isolated by filtration, washed with water and dried in vacuo to yield the title compound 420 mg, m.p. 125°–8°, Found C, 64.16; H, 6.39; N, 11.41%. C$_{42}$H$_{46}$N$_6$O$_8$. 0.7 mol DMF requires C, 64.21; H, 6.37; N, 11.38%. $^1$H NMR (DMSO-d$_6$) δ10.8 (1H, s), 8.5 (1H, d), 8.0 (2H, m), 7.8 (4H, m), 6.9–7.5 (15H, m), 6.8 (1H, d), 4.7 (1H,m), 4.5(1H, m), 4.4 (1H, m), 4.1 (1H, m), 2.6–3.2 (8H, m), 1.2 (9H, s).

EXAMPLE 13

Preparation of
N-1-Adamantyloxycarbonyl-L-tryptophyl-L-3-(2-naphthyl)alanyl-L-aspartyl-L-phenylalaninamide a. N-1-Adamantyloxycarbonyl-L-tryptophyl-L-3-(2-naphthyl)alanyl-β-O-benzyl-L-aspartyl-L-phenylalaninamide To N-t-butyloxycarbonyl-L-tryptophyl-L-3-(2-naphthylalanyl)-β-O-benzyl-L-aspartyl-L-phenylalaninamide (prepared in example 1 d)(0.15 g, 0.176 mmol) was added trifluoroacetic acid (1 ml) and the resulting mixture stirred at room temperature for 15 min. The solution was evaporated in vacuo. The residue was dissolved in dry pyridine (3 ml) and 1-adamantylfluoroformate (35 mg, 0.18 mmol) was added. The mixture was stirred at room temperature for 1 h and then evaporated to approximately 1 ml. This residue was taken up in a 1:1 mixture of 2-propanol and water (10 ml) and the solid formed was filtered, washed with diethyl ether and dried in vacuo to yield the title compound (126 mg), $^1$H NMR (DMSO-d$_6$) δ10.7 (1H, s), 8.5-6.8 (27H, m), 5.1 (2H, s), 4.7 (2H, m), 4.4 (1H, m), 4.1 (1H, m), 3.2-1.2 (23H, m).

b. N-1-Adamantyloxycarbonyl-L-tryptophyl-L-3-(2-naphthyl)alanyl-L-aspartyl-L-phenylalaninamide N-1-Adamantyloxycarbonyl-L-tryptophyl-L-3-(2-naphthyl)alanyl-β-O-benzyl-L-aspartyl-L-phenylalaninamide (0.12 g, 0.13 mmol) was dissolved in methanol (25 ml), acetic acid (5 ml) and 10% palladium on activated carbon catalyst (12 mg) was added. The mixture was stirred under an atmosphere of hydrogen for 24 h and the product isolated by filtration and evaporation, after treatment with chloroform (99 mg), m.p. 194°–7° Found C 60.81; H, 5.82; N, 9.16%. C$_{48}$H$_{52}$N$_6$O$_8$ . 0.5 CHCl$_3$ . 2.9 H$_2$O requires C, 61.13; H, 6.17; N, 8.82%. $^1$H NMR (DMSO-d$_6$) δ10.7 (1H, s), 8.5-6.8 (23H, m), 4.64 (1H, m), 4.57 (1H, m), 4.4 (1H, m), 4.1 (1H, m), 3.4-1.0 (23H, m).

EXAMPLE 14

Preparation of
N-1-Adamantyloxycarbonyl-L-tryptophyl-L-3-(2-naphthyl)alanyl-L-aspartyl-4-methoxyphenethylamide The compound was prepared essentially as described in example 13 except that N-t-butyloxycarbonyl-L-tryptophyl-L3-(2-naphthylalanyl)-β-O-benzyl-L-aspartyl- 4-methoxphenethylamide (prepared as the final intermediate in example 10) was used instead of N-t-butyloxycarbonyl-L-tryptophyl-L-3-(2-naphthylalanyl)-β -O-benzyl-L-aspartyl-L-phenylalaninamide in step a. m.p. 125°–31° [α]$_D$ –40.7° (c=0.27 in ethanol) Found C, 68.34; H, 6.71; N, 8.22%. C$_{48}$H$_{53}$N$_5$O$_8$. 0.9 H2O requires C, 68.34; H, 6.54; N, 8.30%. $^1$H NMR (DMSO-d$_6$) δ10.7 (1H, s), 8.4 (1H, d), 8.0 (1H, d), 7.8 (5H, m), 7.4 (5H, m), 7.1 (4H, m), 6.8 (4H, m), 4.7 (1H, m), 4.6 (1H, m), 4.1 (1H, m), 3.7 (3H, s), 3.2-1.0 (25H, m).

EXAMPLE 15

Preparation of
N-Formyl-L-tryptophyl-L-3-(2-naphthyl)alanyl-L-aspartyl-L-phenylalaninamide The compound was prepared essentially as in example 13 except that acetic formic anhydride was used instead of 1-adamantylfluoroformate in step a. The product was a solid m.p 215°–8°, Found C, 65.83; H, 5.33; N, 11.88%. C$_{38}$H$_{38}$N$_6$O$_7$ requires C, 66.08; H, 5.55; N, 12.17%. $^1$H NMR (DMSO-d$_6$) δ 10.8 (1H, s), 8.4-6.8 (24H, m), 4.5 (3H, m), 4.4 (1H, m), 3.2-2.2 (8H, m).

EXAMPLE 16

Preparation of
N-9-Fluorenylmethoxycarbonyl-L-tryptophyl-L-3-(2-naphthyl)alanyl-L-aspartyl-L-phenylalaninamide a. t-Butyloxycarbonyl-L-3-(2-naphthyl)alanine N-hydroxysuccinimide ester L-3-(2-naphthyl)alanine was treated with one equivalent of BOC ON in the presence of triethylamine, water and dioxane to give the BOC amino acid. This material reacted with N-hydroxysuccinimide and DCCI with DME as solvent to yield, after filtration and evaporation, the title compound.

b. t-Butyloxycarbonyl-L-3-(2-naphthyl)alanyl-β-O-benzyl-L-aspartyl-L-phenylalaninamide t-Butyloxycarbonyl-β-O-benzyl-L-aspartyl-L-phenylalaninamide (prepared in example 1 c) (1.35 g, 2.88 mmol) was dissolved in trifluoroacetic acid (7 ml) and stirred at room temperature for 1 h. The TFA was removed by evaporation and the residue dissolved in DME (20 ml) and triethylamine (1.2 ml) and t-butyloxycarbonyl-L-3-(2-naphthyl)alanine N-hydroxysuccinimide ester (1.19 g, 2.88 mmol) was added. The mixture was stirred at room temperature overnight in which time the product precipitated out. Cold water was added and the mixture was stirred at 0o for 1 h. The product was isolated by filtration, washed with cold water, dried and recrystallised from hot methanol (0.997 g), m.p 195°, $[\alpha]_D$ −9.6° (c=0.83 in methanol) $^1$H NMR (DMSO-$d_6$) δ 8.4 (1H, d), 8.0 (1H, d), 7.8(3H, m), 7.7 (1H, s), 7.4 (9H, m), 7.2 (6H, m), 7.0 (1H, d), 5.1 (2H, s), 4.7 (1H, m), 4.4 (1H, m), 4.2 (1H, m), 3.0 (2H, m), 2.8 (3H, m), 2.6 (1H, m), 1.2 (9H, m).

c. N-9-Fluorenylmethoxycarbonyl-L-tryptophyl-L-3-(2-naphthyl)alanyl-β-O-benzyl-L-aspartyl-L-phenylalaninamide t-Butyloxycarbonyl-L-3-(2-naphthyl)alanyl-β-O-benzyl-L-aspartyl-L-phenylalaninamide (150 mg, 0.23 mmol) was stirred in trifluoroacetic acid (5 ml) for 1 h. The solution was evaporated in vacuo to give upon trituration with ether, a colourless solid. Dry DME (20 ml) was added followed by triethylamine (0.062 ml) and N-9-fluorenylmethoxycarbonyl-L-tryptophan pentafluorophenyl ester (133 mg, 0.23 mmol) and the mixture was stirred at room temperature for 16 h. Water (20 ml) was added and the colourless precipitate was filtered, washed with water, and diethyl ether (2×5 ml) and dried. The title compound was a white solid (118 mg), $^1$H NMR (DMSO-$d_6$) δ10.8 (1H, s), 8.6-6.9 (36H, m), 5.1 (2H, s), 4.7-4.0 (7H, m), 3.6-2.4 (8H, m).

d. N-9-Fluorenylmethoxycarbonyl-L-tryptophyl-L-3-(2-naphthyl)alanyl-L-aspartyl-L-phenylalaninamide N-9-Fluorenylmethoxycarbonyl-L-tryptophyl-L-3-(2-naphthyl)alanyl-β-O-benzyl-L-aspartyl-L-phenylalaninamide (118 mg, 0.12 mmol) was dissolved in ethanol (20 ml) and acetic acid (2 drops) was added. 10% Palladium on activated charcoal (20 mg) was introduced and the mixture stirred at room temperature for 3 days. The mixture was heated to boiling and filtered through a celite pad, washed with hot ethanol and evaporated in vacuo to give a pale beige solid (36 mg), m.p. 233°-236°, $[\alpha]_D$ −8.3° (c=0.12 in DMF), Found C, 66.05; H, 5.39; N, 8.84%. $C_{52}H_{48}N_6O_8$. 1.1 acetic acid. 1.7 $H_2O$ requires C, 66.32; H, 5.73; N, 8.56%. $^1$H NMR (DMSO-$d_6$) δ10.8 (1H, s), 8.5-6.8 (31H, m), 4.6 (1H, m), 4.5 (1H, m), 4.4 (1H, m), 4.2 (1H, m), 4.1 (3H, m), 3.7-2.4 (8H, m).

EXAMPLE 17

Preparation of
N-t-Butyloxycarbonyl-a-methyl-tryptophyl-L-3-(2-naphthyl)alanyl-L-aspartyl-L-phenylalaninamide This was prepared essentially as in example 16 but using the NHS ester of N-t-butyloxycarbonyl-a-methyl-tryptophan instead of N-9-fluorenylmethoxycarbonyl-L-tryptophan pentafluorophenyl ester in step c., m.p. 160°-5°, $[\alpha]_D$ −17.4° (c=0.23 in DMF), Found C, 56.41; H, 5.93; N, 9.21%. $C_{43}H_{48}N_6O_8$. 0.9 dicyclohexylurea. 1.9 $CHCl_3$ requires C, 56.41; H, 5.93; N, 9.21%. $^1$H NMR (DMSO-$d_6$) δ11.0 (1H, s), 8.2-6.8 (23H, m), 4.5 (1H, m), 4.4 (1H, m), 3.7-2.4 (9H, m), 1.4 (9H, s), 1.3 (3H, s).

EXAMPLE 18

Preparation of
N-t-Butyloxycarbonyl-5-fluoro-L-tryptophyl-L-3-(2-naphthyl)alanyl-L-aspartyl-L-phenylalaninamide This was prepared essentially as in example 16 but using the NHS ester of N-t-butyloxycarbonyl-5-fluoro-L-tryptophan instead of N-9-fluorenylmethoxycarbonyl-L-tryptophan pentafluorophenyl ester in step c., m.p. 209°-12°, $[\alpha]_D$ −18.8° (c=0.21 in DMF), Found C, 55.67; H, 5.25; N, 9.14%. $C_{42}H_{45}FN_6O_8$. 0.2 dicyclohexylurea. 1.4 $CHCl_3$ requires C, 55.65; H, 5.20; N, 9.03%. $^1$H NMR (DMSO-$d_6$) δ10.9 (1H, s), 8.6-6.7 (22H, m), 4.6 (1H, m) 4.5 (1H, m), 4.4 (1H, m), 4.1 (1H, m), 3.5-2.0 (8H, m), 1.2 (9H, s).

EXAMPLE 19

Preparation of
N-t-Butyloxycarbonyl-5-methoxy-D,L-tryptophyl-L-3-(2-naphthyl)alanyl-L-aspartyl-L-phenylalaninamide This was prepared essentially as in example 16 but using the NHS ester of N-t-butyloxycarbonyl-5-methoxy-D,L-tryptophan instead of N-9-fluorenylmethoxycarbonyl-L-tryptophan pentafluorophenyl ester in step c., m.p. 198°-203°, $[\alpha]_D$ −42.9° (c=0.49 in DMF) Found C, 62.67; H, 5.99; N, 10.11%. $C_{43}H_{48}N_6O_9$. 1.5 $H_2O$ requires C, 62.95; H, 6.27; N, 10.24%. $^1$H NMR (DMSO-$d_6$) δ10.6 (1H, 2 x s), 8.6-6.6 (22H, m), 4.6 (1H, m) 4.55 (1H, m), 4.4 (1H, m), 4.1 (1H, m), 3.7 (3H, s), 3.4-2.0 (8H, m), 1.2 (9H, s).

EXAMPLE 20

Preparation of
Indole-3-acetamido-L-3-(2-naphthyl)alanyl-L-aspartyl-L-phenylalaninamide This was prepared essentially as in example 16 but using the NHS ester of indole-3-acetic acid instead of N-9-fluorenylmethoxycarbonyl-L-tryptophan pentafluorophenyl ester in step c., m.p. 229°-231°, Found C, 61.75; H, 5.58; N, 10.18%. $C_{36}H_{35}N_5O_6$.2.5 $H_2O$. 0.2 $CHCl_3$ requires C, 61.88; H, 5.77; N, 9.97%. $^1$H NMR (DMSO-$d_6$) δ10.8 (1H, s), 8.5-6.6 (22H, m), 4.6 (1H, m) 4.5 (1H, m), 4.4 (1H, m), 3.4 (2H, s), 3.2-2.3 (6H, m).

EXAMPLE 21

Preparation of
Indole-3-propionamido-L-3-(2-naphthyl)alanyl-L-aspartyl-L-phenylalaninamide This was prepared essentially as in example 16 but using the NHS ester of indole-3-propionic acid instead of N-9-fluorenylmethoxycarbonyl-L-tryptophan pentafluorophenyl ester in step c., m.p. 207°-9°, $[\alpha]_D$ −28° (c=0.18 in methanol) Found C, 65.02; H, 5.77; N, 10.92%. $C_{37}H_{37}N_5O_6$. 1.5 $H_2O$. 0.3 DMF requires C, 65.34; H, 6.09; N, 10.66%. $^1$H NMR (DMSO-$d_6$) δ10.7 (1H, s), 8.4-6.9 (22H, m), 4.6 (1H, m), 4.5 (1H, m), 4.4 (1H, m), 3.2-2.3 (10H, m).

EXAMPLE 22

Preparation of
N-t-Butyloxycarbonyl-D-tryptophyl-L-3-(2-naphthyl)
alanyl-L-aspartyl-L-phenylalaninamide This was prepared essentially as in example 16 but using the NHS ester of N-t-butyloxycarbonyl-D-tryptophan instead of N-9-fluorenylmethoxycarbonyl-L-tryptophan pentafluorophenyl ester in step c., m.p. 208°–9°, $[\alpha]_D$ –26.0° (c=0.11 in methanol) Found C, 66.08; H, 6.04; N, 11.08%. $C_{42}H_{46}N_6O_8$ requires C, 66.13; H, 6.08; N, 11.02%. $^1$H NMR (DMSO-d$_6$) δ 10.7 (1H, s), 8.4-6.6 (23H, m), 4.6 (2H, m), 4.4 (1H, m), 4.1 (1H, m), 3.25-2.2 (8H, m), 1.2 (9H, s).

EXAMPLE 23

Preparation of
N-t-benzyloxycarbonyl-β-alanyl-L-tryptophyl-L-3-
(2-naphthyl)alanyl-L-aspartyl-L-phenylalaninamide The compound of example 1 (128 mg, 0.17 mmol) was treated with trifluoroacetic acid (1 ml) for 15 min. The solution was evaporated and then azeotroped with toluene to remove the final traces of the acid. The residue was dissolved in dry DMF (5 ml) and triethylamine (0.117 ml) and benzyloxycarbonyl-β-alanine p-nitrophenyl ester (58 mg) was introduced. The mixture was allowed to stand at room temperature for 18 h and then evaporated. The residue was taken up in 2-propanol and water (5:2 mixture) and the resulting precipitate filtered, washed with 2-propanol and dried to leave the title compound (100 mg) m.p. 225°–6°, Found C, 66.13; H, 5.82; N, 11.55%. $C_{48}H_{49}N_7O_9$ requires C, 66.42; H, 5.69; N, 11.30%. $^1$H NMR (DMSO-d$_6$) δ10.7 (1H, s), 8.4-6.8 (28H, m), 5.0 (2H, s), 4.5 (4H, m), 3.3-2.1 (12H, m).

EXAMPLE 24

Preparation of
N-t-Butyloxycarbonyl-L-tryptophyl-D-3-
(1-naphthyl)alanyl-L-aspartyl-L-phenylalaninamide The compound was prepared essentially as in example 1 except that D-3-(1-naphthyl)alanine was used in place of L-3-(2-naphthyl)alanine in step 1a. M.p. 178°–80°, $[\alpha]_D$ –35.0 (c=1.0 in DMF); Found C, 63.11; H, 6.27; N, 10.48%. $C_{42}H_{46}N_6O_8 \cdot 2H_2O$ requires C, 63.15; H, 6.31; N, 10.5%. $^1$H NMR (DMSO-d$_6$) δ 10.7 (1H, s), 8.4 (1H, m), 8.2 (1H, d), 8.05 (1H, d), 7.9 (1H, d), 7.75 (1H, d), 6.8–7.6 (17H, m), 6.6 (1H, d), 4.6(2H, m), 4.3 (1H, m), 4.15 (1H, m), 2.1–3.6 (8H, m), 1.25 (9H, s).

EXAMPLE 25

Preparation of
N-t-Butyloxycarbonyl-L-tryptophyl-L-3-(2-naphthyl)
alanyl-L-aspartyl-1-indanylamide a. N-t-Butyloxycarbonyl-L-tryptophyl-L-3-(2-naphthyl)alanyl-β-O-benzyl-L-aspartic acid A solution of N-t-Butyloxycarbonyl-L-tryptophyl-L-3-(2-naphthyl) alanine N'-hydroxysuccinimide ester (prepared as in example 1b) (9.06 g, 13.9 mmol) in dry DMF (20 ml) was added to a suspension of β-O-benzyl-L-aspartic acid (3.10 g, 13.9 mmol) in dry DMF (10 ml) containing triethylamine (4 ml) and the mixture was stirred at room temperature overnight. The clear solution was poured slowly onto a stirred mixture of ice (300 g) and concentrated hydrochloric acid (20 ml) and the resultant white precipitate was filtered, washed with water and dried to yield 8.87 g crude product which was used without further purification. $^1$H NMR (DMSO-d$_6$) δ10.8 (1H, s), 8.6 (1H, d), 8.0 (1H, d), 7.9-6.8 (18H, m), 5.1 (2H, s), 4,7 (2H, m), 4.1 (1H, m), 3.3-2.7 (6H, m), 1.22 (9H, s).

b. N-t-Butyloxycarbonyl-L-tryptophyl-L-3-(2-naphthyl)alanyl-β-O-benzyl-L-aspartic acid N'-hydroxysuccinimide ester A solution of N-t-Butyloxycarbonyl-L-tryptophyl-L-3-(2-naphthyl)alanyl-β-O-benzyl-L-aspartic acid (1.44 g, 2.03 mmol) and N-hydroxysuccinimide (0.23 g, 2.03 mmol) in dry 1,2-dimethoxyethane was cooled in an ice bath. Dicyclohexylcarbodiimide (0.42 g, 2.03 mmol) was added and the mixture stirred at 5° overnight. The precipitated N,N-dicyclohexylurea was removed by filtration and the solvent evaporated in vacuo to give a white solid (1.61 g). The crude product was used for further coupling. $^1$H NMR (DMSO-d$_6$) δ10.8 (1H, s), 9.1 (1H, d), 8.1 (1H, d), 7.9-6.8 (18H, m), 5.1 (3H, m), 4.7 (1H, m), 4.2 (1H, m), 3.3-2.7 (6H, m), 2.8 (4H, s), 1.2 (9H, s).

c. N-t-Butyloxycarbonyl-L-tryptophyl-L-3-(2-naphthyl)alanyl-βO-benzyl-L-aspartyl-1-indanamide A solution of N-t-butyloxycarbonyl-L-tryptophyl-L-3-(2-naphthyl)alanyl-β-O-benzyl-L-aspartic acid N'-hydroxysuccinimide ester (437 mg, 0.55 mmol) and 1-aminoindane (65 mg, 0.57 mmol) in dry 1,2-dimethoxyethane (10 ml) was stirred at room temperature overnight. The mixture was poured into cold water (30 ml) and stirred for 1 h. The resultant precipitate was filtered, washed with 10% aqueous citric acid then with water, and dried in vacuo to yield 363 mg (80%) white solid which was hydrogenolysed without further purification. $^1$H NMR (DMSO-d$_6$) δ10.8 (1H, s), 8.5 (1H, dd), 8.2 (1H, t), 8.0-6.8 (23H, m), 5.3 (1H, m), 5.1 (2H, s), 4.7 (2H, m), 4.1 (1H, m), 3.4-2.7 (8H, m), 2.3 (1H, m), 1.8 (1H, m), 1.2 (9H, m).

d. N-t-Butyloxycarbonyl-L-tryptophyl-L-3-(2-naphthyl)alanyl-L-aspartyl-1-indanylamide N-t-Butyloxycarbonyl-L-tryptophyl-L-3-(2-naphthyl)alanyl-β-O-benzyl-L-aspartyl-1-indanamide was hydrogenolysed following the procedure given in example 1e except that no acetic acid was added. m.p. 133°–136°, $[\alpha]_D$ –20° (c=0.60 in methanol), Found C, 68.91; H, 6.41; N, 9.68%. $C_{42}H_{45}N_5O_7$ requires C, 68.93; H, 6.20; N, 9.57%. $^1$H NMR (DMSO-d$_6$) δ 10,8 (1H, s), 8.4 (1H, t), 8.2 (1H, d), 8.0 (1H, t), 7.9-6.7 (17H, m), 5.3, 4.7, 4.6, 4.1 each (1H, m), 3.4-2.4 (8H, m), 2.3 (1H, m), 1.8 (1H, m), 1.2 (9H, s).

EXAMPLE 26

Preparation of
N-[N-t-Butyloxycarbonyl-L-tryptophyl-L-3-
(2-naphthyl)alanyl-L-aspartyl]-
1,2,3,4-tetrahydroisoquinolinamide a. N-[N-t-Butyloxycarbonyl-L-tryptophyl-L-3-(2-naphthyl)alanyl-β-O-benzyl-L-aspartyl]- 1,2,3,4-tetrahydroisoquinolinamide N-t-Butyloxycarbonyl-L-tryptophyl-L-3-(2-naphthyl)alanyl-β-O-benzyl-L-aspartic acid as prepared in example 25 step a (353 mg, 0.5 mmol), 1,2,3,4-tetrahydroisoquinoline (73 mg, 0.55mmol), diisopropylethylamine (0.175 ml) and PyBOP (260 mg, 0.5 mmol) were dissolved in dichloromethane (5 ml) and stirred at room temperature for 16 h. The solvent was removed under vacuum, the residue taken up in ethyl acetate and the solution washed successively with 5% potassium hydrogensulphate, saturated sodium bicarbonate and brine. After drying (magnesium sulphate) the solvent was removed under vacuum. The residue was purified by column chromatography (silica 95% dichloromethane and 5% methanol) followed by recrystallisation from hexane and ethyl acetate. The title compound was obtained as a white solid 208 mg.

b. N-[N-t-Butyloxycarbonyl-L-tryptophyl-L-3-(2-naphthyl)alanyl-L-aspartyl]- 1,2,3, 4-tetrahydroisoquinolinamide N-[N-t-Butyloxycarbonyl-L-tryptophyl-L-3-(2-naphthyl)alanyl-β-O-benzyl-L-aspartyl]- 1,2,3,4-tetrahydroisoquinolinamide was hydrogenolysed following the procedure given in example 1e except that no acetic acid was added. $[\alpha]_D$ –31° (c=1.0 in methanol), Found C, 66.82; H, 6.24; N, 9.38% $C_{42}H_{45}N_5O_7$. 1.2 $H_2O$ requires C, 66.95; H, 6.34; N, 9.30%. $^1H$ NMR (DMSO-$d_6$) δ 10.8 (1H, s), 8.7 (1H, m), 8.0 (1H, m), 6.9–7.9 (16H, m), 6.8 (1H, m), 5.1 (1H, m), 4.6 (3H, m), 4.1 (1H, m) 2.4–3.8 (10H, m), 1.2 (9H, s).

EXAMPLE 27

Preparation of
N-Butyloxycarbonyl-L-tryptophyl-L-3-(2-naphthyl)
alanyl-L-aspartyl-2-trifluoromethylphenethylamide This was prepared essentially as in example 25 but using 2-trifluoromethylphenethylamine instead of 1-aminoindane in step c. $[\alpha]_D$ –42° (c=1.0 in methanol), Found C, 62.84; H, 5.65; N, 8.89%. $C_{42}H_{44}F_3N_5O_7$. 0.75 $H_2O$ requires C, 62.95; H, 5.72; N, 8.73%. $^1H$ NMR (DMSO-$d_6$) δ10.8 (1H, s), 8.4 (1H, s), 6.8–8.0 (19H, m) 4.7 (1H, m), 4.6 (1H, m), 4.2 (1H, m), 2.5–3.5 (10H, m), 1.2 (9H, s).

EXAMPLE 28

Preparation of
N-t-Butyloxycarbonyl-L-tryptophyl-L-3-(2-naphthyl)
alanyl-L-aspartyl-4-trifluoromethylphenethylamide This was prepared essentially as in example 25 but using 4-trifluoromethylphenethylamine instead of 1-aminoindane in step c. $[\alpha]_D$ +8.0° (c=0.5 in methanol), Found C, 60.65; H, 5.59; N, 8.71%. $C_{42}H_{44}F_3N_5O_7$. 2.25 $H_2O$ requires C, 60.82; H, 6.01; N, 8.44%. $^1H$ NMR (DMSO-$d_6$) δ10.8 (1H, s), 8.4 (1H, d), 8.0 (1H, d), 6.8–7.9 (18H, m), 4.7 (1H, m), 4.5 (1H, m), 4.1 (1H, m), 2.4–3.4 (10H, m) 1.2 (9H, s).

EXAMPLE 29

Preparation of
N-t-Butyloxycarbonyl-L-tryptophyl-L-3-(2-naphthyl)
alanyl-L-aspartyl-trans-2-phenylcyclopropylamide a. N-t-Butyloxycarbonyl-β-O-t-butyl-L-aspartyl-trans-2-phenylcyclopropylamide A solution of trans-2-phenylcyclopropylamine (467 mg, 2.75 mmol), N-t-butyloxycarbonyl-β-O-t-butyl-L-aspartic acid N-hydroxysuccinimide ester (965 mg, 2.5 mmol) and triethylamine (0.3 ml) in DMF (7.5 ml) was stirred for 16 h. After dilution with 2M hydrochloric acid, the product was extracted into ethyl acetate. The solution was dried (MgSO$_4$), the solvent removed under vacuum, and the residue purified by column chromatography (SiO$_2$; dichloromethane, ethyl acetate, 4:1). The title compound was obtained as a white foam, 765 mg (76%). $^1H$ NMR (CDCl$_3$) δ7.2–7.4 (5H, m), 6.8 (1H, s), 5.7 (1H, d), 4.5 (1H, m), 2.9 (2H, m), 2.7 (1H, dd), 2.1 (1H, m), 1.5 (9H, s), 1.1–1.3 (2H, m).

b. N-t-Butyloxycarbonyl-L-tryptophyl-L-3-(2-naphthyl)alanyl-L-aspartyl-trans- 2-phenylcyclopropylamide A solution of N-t-butyloxycarbonyl-β-O-t-butyl-L-aspartyl-trans-2-phenylcyclopropylamide (750 mg, 1.86 mmol) in trifluoroacetic acid (10 ml) was stirred for 1 h. The TFA was removed under vacuum, the residue was dissolved in DMF, triethylamine (0.9 ml) was added, followed by N-t-Butyloxycarbonyl-L-tryptophyl-L-3-(2-naphthyl)alanine NHS ester (prepared in example 1b) (1.112 g, 1.86 mmol). After stirring for 16 h the reaction mixture was diluted with 1M hydrochloric acid. The precipitated title compound was isolated by filtration and drying, 1.09 g (80%). $[\alpha]_D$ –35° (c=1.0 in methanol). Found C, 68.65; H, 6.43; N, 9.59%. $C_{42}H_{45}N_5O_7$ requires C, 68.93; H, 6.20; N, 9.57%. $^1H$ NMR (DMSO-$d_6$) δ10.8 (1H, s), 8.4 (1H, d), 6.8–8.1 (20H, m), 4.6 (1H, m), 4.55 (1H, m), 4.2 (1H, m), 2.6–3.4 (7H, m), 1.9 (1H, m), 1.2 (9H, s), 1.1 (2H, m).

EXAMPLE 30

Preparation of
N-t-Butyloxycarbonyl-L-tryptophyl-L-3-
(2-naphthyl)alanyl-L-aspartyl-
4-nitrophenethylamide Prepared essentially as in example 29 but using 4-nitrophenethylamine instead of trans-2-phenylcyclopropylamine in step a. $[\alpha]_D$ –28° (c=1.0 in methanol). Found C, 62.03; H, 5.98; N, 10.33%. $C_{41}H_{44}N_6O_9$. 1.7 $H_2O$ requires C, 61.91; H, 6.01; N, 10.56%. $^1H$ NMR (DMSO-$d_6$) δ10.8 (1H, s), 8.4 (1H, d), 6.8–8.1 (19H, m), 4.7 (1H, m), 4.5 (1H, m), 4.1 (1H, m), 2.6–3.5 (10H, m), 1.2 (9H, s).

EXAMPLE 31

Preparation of
N-t-Butyloxycarbonyl-L-tryptophyl-L-3-(2-naphthyl)
alanyl-L-aspartyl-trans- 2-phenylcyclopentylamide
(diastereomer 1)

a. N-t-Butyloxycarbonyl-L-tryptophyl-L-3-(2-naphthyl)alanyl-β-O-benzyl-L-aspartyl-trans- 2-phenylcyclopentylamide A solution of N-t-Butyloxycarbonyl-L-tryptophyl-L-3-(2-naphthyl)alanyl-β-O-benzyl-L-aspartic acid N'-hydroxysuccinimide ester (prepared in example 25b) (400 mg, 0.5 mmol) and trans-2-phenylcyclopentylamine (97 mg, 0.6mmol) (J.A.C.S. 88, 2870, 1966) in DMF (3 ml) was stirred for 16 h, then diluted with 1M hydrochloric acid. The white solid precipitate was filtered off and dried to give a mixture of diastereomers, 390 mg (92%). The diastereomers were separated by column chromatography (SiO$_2$; dichloromethane, ethyl acetate 4:1) to give:

Diastereomer A $R_f$=0.37; $^1H$ NMR (DMSO-$d_6$) δ10.8 (1H, s), 8.4 (1H, d), 8.0 (1H, d), 6.8–7.9 (24H, m), 5.0 (2H, s), 4.6 (1H, m), 4.5 (1H, m), 4.1 (1H, m), 2.4–3.3 (7H, m), 2.0 (3H, m), 1.7 (3H, m), 1.5 (1H, m), 1.2 (9H, s).

Diastereomer B $R_f$=0.29; $^1H$ NMR (DMSO-$d_6$) δ10.8 (1H, s), 8.4 (1H, d), 6.8–7.9 (25H, m), 5.1 (2H, s), 4.6(2H, m), 4.1 (1H, m), 2.4–3.2 (7H, m), 2.0 (3H, m) 1.7 (3H, m), 1.5 (1H, m), 1.2 (9H, s).

b. N-t-Butyloxycarbonyl-L-tryptophyl-L-3-(2-naphthyl)alanyl-L-aspartyl-trans- 2-phenylcyclopentylamide (diastereomer 1)

Diastereomer A was hydrogenolysed using essentially the conditions in example 1e. $[\alpha]_D$ –28° (c=0.5 in methanol), Found C, 68.02; H, 6.61; N, 9.37%; $C_{44}H_{49}N_5O_7$. H2O requires C, 67.94; H, 6.61; N, 9.00%. $^1H$ NMR (DMSO-$d_6$)

δ10.8 (1H, s), 8.4 (1H, d), 6.8–7.9 (19H, m), 4.6 (1H, m), 4.5 (1H, m), 4.1 (1H, m), 4.05 (1H, t), 2.2–3.4 (8H, m), 1.4-2.1 (6H, m), 1.2 (9H, s).

EXAMPLE 32

Preparation of
N-t-Butyloxycarbonyl-L-tryptophyl-L-3-(2-naphthyl)
alanyl-L-aspartyl-trans- 2-phenylcyclopentylamide
(diastereomer 2)

Diastereomer B (prepared in example 31a) was hydrogenolysed using essentially the conditions in example 1e. $[\alpha]_D$ −66° (c=0.5 in methanol), Found C, 68.08; H, 6.61; N, 9.15%. $C_{44}H_{49}N_5O_7$. 0.7 $H_2O$ requires C, 68.32; H, 6.69; N, 9.46%. $^1$H NMR (DMSO-$d_6$) δ10.8 (1H, s), 8.4 (1H, d), 6.8–7.9 (19H, m), 4.6 (1H, m), 4.5 (1H, m), 4.1 (1H, m), 4.05 (1H, t), 2.2–3.4 (8H, m), 1.4–2.1 (6H, m), 1.2 (9H, s).

EXAMPLE 33

Preparation of
N-t-Butyloxycarbonyl-L-tryptophyl-L-3-(2-naphthyl)
alanyl-L-aspartyl-cis- 2-phenylcyclopentylamide
(diastereomer 1)

a. Preparation of N-t-Butyloxycarbonyl-L-tryptophyl-L-3-( 2-naphthyl)alanyl-β-O-benzyl-L-aspartyl-cis-2-phenylcyclopentylamide A mixture of diastereomers was prepared essentially as in example 31a but substituting cis-2-phenylcyclopentylamine for trans-2-phenylcyclopentylamine. The diastereomers separated by column chromatography (SiO$_2$; dichloromethane, ethylacetate 7:3),to give:

Diastereomer C $R_f$=0.40; $^1$H NMR (DMSO-$d_6$) δ10.8 (1H, s), 8.3 (1H, d), 6.8–7.9 (25H, m), 5.0 (2H, m), 4.6 (1H, m), 4.5 (2H, m), 4.1 (1H, m), 2.4–3.4 (7H, m), 1.4-2.1 (6H, m), 1.3 (9H, s).

Diastereomer D $R_f$=0.33; $^1$H NMR (DMSO-$d_6$) δ10.8 (1H, s), 8.2 (1H, d), 6.8–7.9 (25H, m), 5.0 (2H, m), 4.6 (1H, m), 4.5 (1H, m), 4.4 (1H, m), 4.1 (1H, m), 2.4–3.4 (7H, m), 1.4–2.1 (6H, m), 1.2 (9H, s).

b. N-t-Butyloxycarbonyl-L-tryptophyl-L-3-(2-naphthyl)alanyl-L-aspartyl-cis- 2-phenylcyclopentylamide (diastereomer 1)

Diastereomer C was hydrogenolysed using essentially the same conditions as step 1e. $[\alpha]_D$ −43° (c=1.0 in methanol), Found C, 68.54; H, 6.42; N, 9.33%. $C_{44}H_{49}N_5O_7$. 0.5 $H_2O$ requires C, 68.73; H, 6.55; N, 9.11%. $^1$H NMR (DMSO-$d_6$) δ10.8 (1H, s), 8.3 (1H, d), 6.9–7.9 (18H, m), 6.8 (1H, d), 5.6 (1H, d), 4.6 (1H, m), 4.5 (1H, m), 4.4 (1H, m), 4.1 (1H, m), 2.4–3.4 (7H, m), 1.0–2.1 (6H, m), 1.3 (9H, s).

EXAMPLE 34

Preparation of
N-t-Butyloxycarbonyl-L-tryptophyl-L-3-(2-naphthyl)
alanyl-L-aspartyl-cis-2-phenylcyclopentylamide
(diastereomer 2)

Diastereomer D (prepared in example 33a) was hydrogenolysed using essentially the conditions in example 1e. $[\alpha]_D$=−34° (c=1.0 in methanol), Found C, 66.24; H, 6.55; N, 8.71%. $C_{44}H_{49}N_5O_7$. 2$H_2O$ requires C, 66.39; H, 6.71; N, 8.80%. $^1$H NMR (DMSO-$d_6$) δ10.8 (1H, s), 8.1 (1H, d), 6.9–7.9 (19H, m), 6.8 (1H, d), 4.6 (1H, m), 4.4 (2H, m), 4.1 (1H, m), 2.4–3.4 (7H, m), 1.1–2.1 (6H, m), 1.3 (9H, s).

EXAMPLE 35

Preparation of
N-t-Butyloxycarbonyl-L-tryptophyl-L-3-(2-naphthyl)
alanyl-L-aspartyl-1-adamantylmethylamide The material was prepared essentially as in example 1 but using N-t-butyloxycarbonyl-β-O-benzyl-L-aspartyl-1-adamantylmethylamide (prepared from the coupling of the NHS ester of N-t-butyloxycarbonyl-β-O-benzyl-L-aspartic acid with 1-adamantylmethylamine in DME) instead of N-t-butyloxycarbonyl-β-O-benzyl-L-aspartyl-L-phenylalaninamide in step d. m.p. 142°–6°, $[\alpha]_D$ −34.1° (c=0.56 in ethanol) Found C, 68.21; H, 7.11; N, 9.01%. $C_{44}H_{53}N_5O_7$. 0.5 $H_2O$ requires C, 68.37; H, 7.04; N, 9.06%. $^1$H NMR (DMSO-$d_6$) δ10.8 (1H, s), 8.4 (1H, d), 8.0 (1H, d), 7.7 (5H, m), 7.4 (4H, m), 7.3 (1H, d), 6.9 (3H, m), 6.8 (1H, d), 4.7 (1H, m), 4.6 (1H, m), 4.1 (1H, m), 3.1-2.6 (8H, m), 1.8 (3H, s), 1.6 (6H, s), 1.4 (6H, s), 1.2 (9H, s).

EXAMPLE 36

Preparation of
N-t-Butyloxycarbonyl-L-tryptophyl-L-3-(2-naphthyl)
alanyl-L-aspartyl-L-3-cyclohexylalaninamide The material was prepared essentially as in example 1 but using N-t-butyloxycarbonyl-β-O-benzyl-L-aspartyl-L-3-cyclohexylalaninamide) (prepared from the coupling of the NHS ester of N-t-butyloxycarbonyl-β-O-benzyl-L-aspartic acid with L-3-cyclohexylalaninamide in DME) instead of N-t-butyloxycarbonyl-β-O-benzyl-L-aspartyl-L-phenylalaninamide in step d. m.p 181°–4°, $[\alpha]_D$ −28.0° (c=0.36 in ethanol) Found C, 65.43; H, 6.71; N, 10.76%. $C_{42}H_{52}N_6O_7$ requires C, 65.61; H, 6.82; N, 10.93%. $^1$H NMR (DMSO-$d_6$) δ10.8 (1H, s), 8.6 (1H, d), 8.0 (1H, d), 7.8 (4H, m), 7.4 (4H, m), 7.3 (2H, m), 7.0 (4H, m), 6.8 (1H, d), 4.7 (1H, m) 4.6 (1H, m), 4.1 (1H, m), 3.1-2.6 (8H, m), 1.8 (3H, s), 1.6 (6H, s), 1.4 (6H, s), 1.2 (9H, s).

EXAMPLE 37

Preparation of
N-t-Butyloxycarbonyl-L-tryptophyl-L-3-(2-naphthyl)
alanyl-L-aspartyl-2,4-dichlorophenethylamide The material was prepared essentially as in example 1 but using N-t-butyloxycarbonyl-β-O-benzyl-L-aspartyl-2,4-dichlorophenylethylamide (prepared from the coupling of the NHS ester of N-t-butyloxycarbonyl-β-O-benzyl-L-aspartic acid with 2,4-dichlorophenylethylamine in DME) instead of N-t-butyloxycarbonyl-β-O-benzyl-L-aspartyl-L-phenylalaninamide in step d. m.p. 109°–111°, $[\alpha]_D$ −30.2° (c=0 73 in methanol) Found C, 61.22; H, 5.69; N, 8.61%. $C_{41}H_{43}N_5O_7.H_2O$ requires C, 61.04; H, 5.62; N, 8.68%. $^1$H NMR (DMSO-$d_6$) δ10.8 (1H, s), 8.4 (1H, d), 8.0 (1H, d), 7.8 (5H, m), 7.4 (9H, m), 7.0 (3H, m), 4.6 (1H, m), 4.1 (1H, m), 3.2 (4H, m), 2.7 (6H, m), 1.2 (9H, s).

EXAMPLE 38

Preparation of
N-t-Butyloxycarbonyl-L-tryptophyl-L-3-(2-naphthyl)
alanyl-L-aspartyl-4-hydroxyphenethylamide The compound was prepared essentially as in example 1 except that N-t-butyloxycarbonyl-β-O-benzyl-L-aspartyl-4-hydroxyphenethylamide (prepared by coupling N-t-butyloxycarbonyl-β-O-benzyl-L-aspartic acid N'-hydroxysuccinimide ester with 4-hydroxyphenethylamine in DME) was used in place of N-t-butyloxycarbonyl-β-O-benzyl-L-aspartyl-L-phenylalaninamide in step d. m.p. 154°–157°, $[\alpha]_D$ –20° (c=0.4 in methanol), $^1$H NMR (DMSO-d$_6$) δ10.9 (1H, s), 9.2 (1H, s), 8.5 (1H, d), 8.1 (2H, m), 7.8 (4H, m), 7.4 (4H, m), 7.3 (1H, d), 7.0 (4H, m), 6.9 (2H, d), 6.7 (1H, d), 6.6 (2H, d), 4.7, 4.5, 4.1 each (1H, m), 3.1 (2H, m), 3.4-2.4 (6H, m), 2.4 (2H, m), 1.2 (9H, s).

EXAMPLE 39

Preparation of
N-t-Butyloxycarbonyl-L-tryptophyl-L-3-(2-naphthyl)alanyl-L-aspartyl-3-methylphenethylamide The compound was prepared essentially as in example 1 except that N-t-butyloxycarbonyl-β-O-benzyl-L-aspartyl-3-methylphenethylamide (prepared by coupling N-t-butyloxycarbonyl-β-O-benzyl-L-aspartic acid N'-hydroxysuccinimide ester with 3-methylphenethylamine in DME) was used in place of N-t-butyloxycarbonyl-β-O-benzyl-L-aspartyl-L-phenylalaninamide in step d., m.p. 188°–190°, $[\alpha]_D$ –43° (c=0.3 in methanol), Found C, 67.51; H, 6.52; N, 9.45%. $C_{42}H_{47}N_5O_7$. 0.7 H$_2$O requires C, 67.58; H, 6.53; N, 9.38%. $^1$H NMR (DMSO-d$_6$) δ10.8 (1H, s), 8.4 (1H, d ), 8.0 (1H, d ), 7.8 (5H, m), 7.4 (4H, m), 7.3 (1H, d), 7.0 (7H, m), 6.8 (1H, d), 4.6, 4.5, 4.1 each (1H, m), 3.4-2.4 (10H, m), 2.2 (3H, s), 1.2 (9H, s).

EXAMPLE 40

Preparation of
N-t-Butyloxycarbonyl-L-tryptophyl-L-3-(2-naphthyl)alanyl-L-aspartyl-2-methoxyphenethylamide The compound was prepared as in example 1 except that N-t-butyloxycarbonyl-β-O-benzyl-L-aspartyl-2-methoxyphenethylamide (prepared by coupling N-t-butyloxycarbonyl-β-O-benzyl-L-aspartic acid N'-hydroxysuccinimide ester with 2-methoxyphenethylamine in DME) was used in place of N-t-butyloxycarbonyl-β-O-benzyl-L-aspartyl-L-phenylalaninamide in step d. m.p. 113°–114°; $[\alpha]_D$ –35.5° (c=0.45 in methanol), Found C, 65.95; H, 6.35; N, 9.12%. $C_{42}H_{47}N_5O_7$. 0.8 mol H$_2$O requires C, 66.00; H, 6.41; N, 9.16%. $^1$H NMR (DMSO-d$_6$) δ10.8 (1H, s), 8.4 (1H, d), 8.0 (1H, d), 7.8-6.7 (18H, m), 4.6, 4.5, 4.1 each (1H, m), 3.7 (3H, s), 3.1 (2H, m), 3.1-2.4 (8H, m), 1.2 (9H, s).

EXAMPLE 41

Preparation of
N-t-Butyloxycarbonyl-L-tryptophyl-L-3-(2-naphthyl)alanyl-L-aspartyl-3,4-dimethoxyphenethylamide The compound was prepared as in example 1 except that N-t-butyloxycarbonyl-β-O-benzyl-L-aspartyl-3,4-dimethoxyphenethylamide (prepared by coupling N-t-butyloxycarbonyl-β-O-benzyl-L-aspartic acid N'-hydroxysuccinimide ester with 3,4-dimethoxyphenethylamine in DME) was used in place of N-t-butyloxycarbonyl-β-O-benzyl-L-aspartyl-L-phenylalaninamide in step d. m.p. 119°–122°, $[\alpha]_D$ –42° (c=0.45, in methanol), Found C, 66.29; H, 6.45; N, 8.96%. $C_{43}H_{49}N_5O_9$ requires C, 66.22; H, 6.33; N, 8.98%. $^1$H NMR (DMSO-d$_6$) δ10.8 (1H, s), 8.4 (1H, d), 8.00 (1H, d), 7.9-6.5 (17H, m), 4.6, 4.5, 4.1 each (1H, m), 3.7 (3H, s), 3.6 (3H, s), 3.5-2.4 (10H, m), 1.2 (9H, s).

EXAMPLE 42

Preparation of
N-t-Butyloxycarbonyl-L-tryptophyl-L-3-(2-naphthyl)alanyl-L-aspartyl-3,4-dichlorophenethylamide The compound was prepared as in example 1 except that N-t-butyloxycarbonyl-β-O-benzyl-L-aspartyl-3,4-dichlorophenethylamide (prepared by coupling N-t-butyloxycarbonyl-β-O-benzyl-L-aspartic acid N'-hydroxysuccinimide ester with 3,4-dichlorophenethylamine in DME) was used in place of N-t-butyloxycarbonyl-β-O-benzyl-L-aspartyl-L-phenylalaninamide in step d. m.p. 154°–159°, $[\alpha]_D$ –26.5° (c=0.34 in methanol), Found C, 59.21; H, 5.55; N, 8.33%. $C_{41}H_{43}Cl_2N_5O_7$. 2.2 H$_2$O requires C, 59.43; H, 5.77; N, 8.45%. $^1$H NMR (DMSO-d$_6$) δ10.8 (1H, s), 8.4 (1H, d), 8.0 (1H, d), 7.9-6.8 (17H, m), 4.6, 4.5, 4.1 each (1H, m), 3.4-2.4 (10H, m), 1.2 (9H, s).

EXAMPLE 43

Preparation of
N-t-Butyloxycarbonyl-L-tryptophyl-L-3-(2-naphthyl)alanyl-L-aspartyl-2-(5, 6, 7, 8-tetrahydronaphthyl)ethylamide The compound was prepared essentially as in example 1 except that N-t-butyloxycarbonyl-β-O-benzyl-L-aspartyl-2-(5,6,7,8-tetrahydronaphthyl)ethylamide (prepared by coupling N-t-butyloxycarbonyl-β-O-benzyl-L-aspartic acid N'-hydroxysuccinimide ester with 2-(5,6,7,8-tetrahydronaphthyl)ethylamine in DME) was used in place of N-t-butyloxycarbonyl-β-O-benzyl-L-aspartyl-L-phenylalaninamide in step d. m.p. 120°–123°, $[\alpha]_D$ –15° (c=0.33 in methanol) Found C, 67.41; H, 6.65; N, 8.96%. $C_{45}H_{51}N_5O_7$. 1.4 mol H$_2$O requires C, 67.62; H, 6.79; N, 8.76%. $^1$H NMR (DMSO-d$_6$) δ10.8 (1H, s), 8.4 (1H, d), 8.0 (1H, d), 7.9-6.7 (17H, m), 4.6, 4.5, 4.1 each (1H, m), 3.4-2.4 (12H, m), 3.1 (2H, m), 1.7 (4H, m), 1.2 (9H, s).

EXAMPLE 44

Preparation of
N-t-Butyloxycarbonyl-L-tryptophyl-L-3-(2-naphthyl)alanyl-L-aspartyl-2-(4-pyridyl)ethylamide The compound was prepared essentially as in example 1 except that N-t-butyloxycarbonyl-β-O-benzyl-L-aspartyl-2-(4-pyridyl)ethylamide (prepared by coupling N-t-butyloxycarbonyl-β-O-benzyl-L-aspartic acid N'-hydroxysuccinimide ester with 2-(4-pyridyl)ethylamine in DME) was used in place of N-t-butyloxycarbonyl-β-O-benzyl-L-aspartyl-L-phenylalaninamide in step d. m.p. 159°–164°, $[\alpha]_D$ –43° (c=0.44 in methanol), Found C, 63.92; H, 6.16; N, 10.65%. $C_{40}H_{44}N_6O_7$. 1.4 mol H$_2$O. 0.3 mol ethyl acetate requires C, 64.06; H, 6.42; N, 10.88%. $^1$H NMR (DMSO-d$_6$) δ10.8 (1H, s), 8.42 (2H, d), 8.40 (1H, d), 8.0 (1H, d), 7.9-6.8 (16H, m), 4.6, 4.5, 4.1 each (1H, m), 3.2 (2H, m), 3.3-2.4 (6H, m), 2.7 (2H, t),1.2 (9H, s).

EXAMPLE 45

N-t-Butyloxycarbonyl-L-N$^{in}$-methyltryptophyl-L-3-(2-naphthyl)alanyl-L-aspartyl-L-phenylalaninamide This was prepared essentially as described in example 16 with the exception that N-t-butyloxycarbonyl-L-N$^{in}$-methyltryptophan N-hydroxysuccinimide ester was used in place of N-fluorenylmethoxycarbonyl-L-tryptophan pentafluorophenyl ester in step c., m.p 202°–205°, [α]$_D$ –12.5° (c=0.4 in DMSO), Found C, 66.31; H, 6.27; N, 10.91%; C$_{43}$H$_{48}$N$_6$O$_8$ requires C, 66.48; H, 6.23; N, 10.82%; $^1$H NMR (DMSO-d$_6$) δ8.5 (1H, d), 8.0-6.6 (23H, m), 4.6 (1H, m), 4.5 (1H, m), 4.4 (1H, m), 4.1 (1H, m), 3.6 (3H, s), 3.3-2.6 (8H, m), 1.2 (9H, s).

EXAMPLE 46

Preparation of N-t-Butyloxycarbonyl-L-tryptophyl-L-3-(2-naphthyl) alanyl-L-aspartyl-4-aminophenethylamide The compound was prepared essentially as in example 1 except that N-t-butyloxycarbonyl-β-O-benzyl-L-aspartyl-4-aminophenethylamide (prepared by coupling N-t-butyloxycarbonyl-β-O-benzyl-L-aspartic acid N'-hydroxysuccinimide ester with 4-aminophenethylamine) was used in place of N-t-butyloxycarbonyl-β-O-benzyl-L-aspartyl-L-phenylalaninamide in step d. m.p. 149°–152°, [α]$_D$ –20° (c=0.49 in methanol), Found C, 65.89; H, 6.33; N, 10.79%. C$_{41}$H$_{46}$N$_6$O$_7$. 0.66 mol ethyl acetate requires C, 66.10; H, 6.52; N, 10.60%. $^1$H NMR (DMSO-d$_6$) δ10.8 (1H, s), 8.4 (1H, d), 8.0 (1H, d), 7.9-6.8 (14H, m), 6.8 (2H, m), 6.4 (2H, m), 4.6, 4.5, 4.1 each (1H, m), 3.3-2.3 (10H, m), 1.2 (9H, s).

EXAMPLE 47

Preparation of N-t-Butyloxycarbonyl-L-tryptophyl-L-3-(2-naphthyl) alanyl-L-aspartyl-4-fluorophenethylamide The compound was prepared as in example 1 except that N-t-butyloxycarbonyl-β-O-benzyl-L-aspartyl-4fluorophenethylamide (prepared by coupling N-t-butyloxycarbonyl-β-O-benzyl-L-aspartic acid N'-hydroxysuccinimide ester with 4-fluorophenethylamine) was used in place of N-t-butytoxycarbonyl-β-O-benzyl-L-phenylalaninamide in step d. m.p.118°–122°, [α]$_D$ –39° (c=0.98 in methanol), Found C, 66.57; H, 6.21; N, 9.42%. C$_{41}$H$_{44}$FN$_5$O$_7$ requires C, 66.74; H, 6.01; N, 9.49%. $^1$H NMR (DMSO-d$_6$) δ10.7 (1H, s), 8.4 (1H, d), 8.0 (1H, d), 7.9-6.7 (18H, m), 4.6, 4.5, 4.1 each (1H, m), 3.2-2.5 (10H, m), 1.2 (9H, s).

EXAMPLE 48

Preparation of N-t-Butyloxycarbonyl-L-tryptophyl-L-3-(2-naphthyl) alanyl-L-aspartyl-2-N-( 6,7-dimethoxy-1,2,3,4-tetrahydro)isoquinolinamide The compound was prepared essentially as in example 1 except that N-t-butyloxycarbonyl-β-O-benzyl-L-aspartyl-2-N-(6,7-dimethoxy-1,2,3,4-tetrahydro)isoquinolinamide (prepared by coupling N-t-butyloxycarbonyl-β-O-benzyl-L-aspartic acid with 6,7-dimethoxy-1,2,3,4-tetrahydroisoquinoline in DME using DCCI and 1-hydroxybenzotriazole(HOBT)) was used in place of N-t-butyloxycarbonyl-β-O-benzyl-L-aspartyl-L-phenylalaninamide in step d. m.p. 125°–128°; [α]$_D$ –23° (c=0.31 in methanol), Found C, 63.67; H, 6.28; N, 8.18%. C$_{44}$H$_{49}$N$_5$O$_9$. 2.27 mol H$_2$O requires C, 63.46; H, 6.42; N, 8.41%. $^1$H NMR (DMSO-d$_6$) δ10.8 (1H, s), 8.7 (1H, d ), 7.9 (1H, d ), 7.9-6.5 (15H, m), 5.0 (1H, m), 4.6 (1H, m), 4.4 (2H, m), 4.1 (1H, m), 3.7 (3H, s), 3.6 (3H, s), 3.7-2.6 (10H, m), 1.2 (9H, s).

EXAMPLE 49

Preparation of N-t-Butyloxycarbonyl-L-tryptophyl-L-3-(2-naphthyl) alanyl-L-aspartyl-4-sulphonamidophenethylamide The compound was prepared essentially as in example 25 except that 4-(2-aminoethyl)benzenesulphonamide was used in place of 1-aminoindane in step c and a 5:1 mixture of 1,2-dimethoxyethane and N,N-dimethylformamide was employed as solvent in this step. m.p. 132°–135°, [α]$_D$ –42° (c=0.69 in methanol), Found C, 59.53; H, 5.91; N, 10.16%. C$_{41}$H$_{46}$N$_6$O$_9$S requires C, 61.64; H, 5.80; N, 10.52%. $^1$H NMR (DMSO-d$_6$) δ 10.8 (1H, s), 8.4 (1H, d), 8.0 (1H, d), 7.9-6.8 (20H, m), 4.6, 4.5, 4.1 each (1H, m), 3.3-2.5 (10H, m), 1.2 (9H, s).

EXAMPLE 50

Preparation of N-t-Butyloxycarbonyl-L-tryptophyl-L-3-(2-naphthyl) alanyl-L-aspartyl-3-trifluoromethylphenethylamide The compound was prepared essentially as in example 25 except that 3-trifluoromethylphenethylamine was used in place of 1-aminoindane in step c. m.p. 179°–183°, [α]$_D$ –40° (c=0.77 in methanol), Found C, 63.13; H, 5.68; N, 8.96%. C$_{42}$H$_{44}$F$_3$N$_5$O$_7$. 0.5 mol H$_2$O requires C, 63.31; H, 5.69; N, 8.79%. $^1$H NMR (DMSO-d$_6$) δ10.8 (1H, s), 8.4 (1H, d), 8.0 (1H, d), 7.9-6.8 (18H, m), 4.6, 4.5, 4.1 each (1H, m), 3.4-2.5 (10H, m), 1.2 (9H, s).

EXAMPLE 51

Preparation of N-t-Butyloxycarbonyl-L-tryptophyl-L-3-(2-naphthyl) alanyl-L-aspartyl-4-methoxybenzamide The compound was prepared essentially as in example 25 except that 4-methoxybenzylamine was used in place of 1-aminoindane in step c and a 2.5:1 mixture of methanol and THF was used as solvent in step d. m.p. 145°–149°, [α]$_D$ –24° (c=0.78 in methanol), Found C, 65.35; H, 6.22; N, 9.45%. C$_{41}$H$_{45}$N$_5$O$_8$. 0.9 mol H$_2$O requires C, 65.48; H, 6.27; N, 9.31%. $^1$H NMR (DMSO-d$_6$) δ10.8 (1H, s), 8.5 (1H, d ), 8.0 (1H, d ), 8.2 (1H, t), 7.9-6.8 (17H, m), 4.6 (2H, m), 4.2 (3H, m), 3.7 (3H, s), 3.3-2.4 (6H, m), 1.2 (9H, s).

EXAMPLE 52

Preparation of N-t-Butyloxycarbonyl-L-tryptophyl-L-3-(2-naphthyl) alanyl-D-aspartyl-4-fluorophenethylamide The compound was prepared essentially as in example 1 except that N-t-butyloxycarbonyl-β-O-benzyl-L-aspartyl-L-4-fluorophenethylamide (prepared by coupling N-t-butyloxycarbonyl-β-O-benzyl-D-aspartic acid with 4-fluorophenethylamine in DME using DCCI and HOBT) was used in place of N-t-butyloxycarbonyl-β-O-benzyl-L-aspartyl-L-phenylalaninamide in step d. m.p. 109°–114°; [α]$_D$ –9° (c=0.43 in methanol), Found C, 65.41; H, 6.12; N, 9.33%. C$_{41}$H$_{44}$FN$_5$O$_7$. 0.8 mol H$_2$O requires C, 65.43; H, 6.11; N, 9.31%. $^1$H NMR (DMSO-d$_6$) δ10.8 (1H, s), 8.5 (1H, d), 8.10 (1H, d), 8.0-6.8 (18H, m), 4.6, (2H, m), 4.2 (1H ,m), 3.2 (2H, m), 3.1-2.3 (6H, m), 2.7 (2H, t), 1.2 (9H, s).

EXAMPLE 53

Preparation of
N-t-Butyloxycarbonyl-L-tryptophyl-L-3-(2-naphthyl)alanyl-L-aspartyl-2-indanylamide The compound was prepared essentially as in example 25 except that 2-aminoindane hydrochloride with triethylamine was used in place of 1-aminoindane in step c and a 2:1 mixture of methanol and THF was used as solvent in step d. m.p. 177°–183°, $[\alpha]_D$ –17° (c=0.41 in methanol), Found C, 67.46; H, 6.33; N, 9.31%. $C_{42}H_{45}N_5O_7$. 0.9 mol H2O requires C, 67.42; H, 6.31; N, 9.36%. $^1$H NMR (DMSO-$d_6$) δ 10.8 (1H, s), 8.4 (1H, d), 8.1 (1H, d), 8.0 (1H, d), 7.9-6.8 (17H, m), 4.6, 4.5, 4.4, 4.1 each (1H, m), 3.2-2.5 (10H, m), 1.2 (9H, s).

EXAMPLE 54

Preparation of
N-t-Butyloxycarbonyl-L-tryptophyl-L-3-(2-naphthyl)alanyl-L-aspartyl-2-fluorophenethylamide The compound was prepared as in example 25 except that 2-fluorophenethylamine was used in place of 1-aminoindane in step c and a 2:1 mixture of methanol and THF was used as solvent in step d. m.p. 156°–159°, $[\alpha]_D$ –41.5° (c=0.53 in methanol), Found C, 64.27; H, 6.12; N, 9.50%. $C_{41}H_{44}FN_5O_7$. 1.4 mol $H_2O$ requires C, 64.58; H, 6.12; N, 9.12%. $^1$H NMR (DMSO-$d_6$) δ10.8 (1H, s), 8.4 (1H, d), 8.0 (1H, d), 8.0-6.8 (18H, m), 4.7, 4.5, 4.1 each (1H, m), 3.2 (2H, m), 3.2-2.5 (6H,), 2.7 (2H, t), 1.2 (9H, s).

EXAMPLE 55

Preparation of
N-t-Butyloxycarbonyl-L-tryptophyl-L-3-(2-naphthyl)alanyl-L-aspartyl-2,4,6-trimethoxyphenethylamide The compound was prepared essentially as in example 25 except that 2,4,6-trimethoxyphenethylamine was used in place of 1-aminoindane in step c and a 5:1 mixture of methanol and THF was used as solvent in step d. m.p. 179°–182°, $[\alpha]_D$ –27° (c=0.3 in methanol), Found C, 63.05; H, 6.44; N, 8.40%. $C_{44}H_{51}N_5O_{10}$. 1.5 mol $H_2O$ requires C, 63.12; H, 6.51; N, 8.36%. $^1$H NMR (DMSO-$d_6$) δ10.8 (1H, s), 8.4 (1H, d), 8.0 (1H, d), 7.9-6.8 (14H, m), 4.7, 4.5, 4.1 each (1H, m), 3.7 (9H, s), 3.3-2.5 (10H, m), 1.2 (9H, s).

EXAMPLE 56

Preparation of
N-t-Butyloxycarbonyl-L-tryptophyl-L-3-(2-naphthyl)alanyl-L-aspartyl-3-methoxyphenethylamide The compound was prepared essentially as in example 25 except that 3-methoxyphenethylamine was used in place of 1-aminoindane in step c. m.p. 167°–172°, $[\alpha]_D$ –31° (c=0.49 in methanol), Found C, 65.78; H, 6.36; N, 9.37%. $C_{42}H_{47}N_5O_8$. 0.8 mol $H_2O$ requires C, 65.98; H, 6.41; N, 9.46%. $^1$H NMR (DMSO-$d_6$) δ10.8 (1H, s), 8.4 (1H, d), 8.0 (1H, d), 7.9-6.7 (18H, m), 4.6, 4.5, 4.1 each (1H, m), 3.7 (3H, s), 3.5-2.6 (10H, m), 1.2 (9H, s).

EXAMPLE 57

Preparation of
N-t-Butyloxycarbonyl-L-tryptophyl-L-2-methyl-3-(2-naphthyl)alanyl-L-aspartyl-L-phenylalaninamide a. N-t-Butyloxycarbonyl-L-2-methyl-3-(2-naphthyl)alanine L-2-methyl-3-(2-naphthyl)alanine (0.53 g, 2.3 mmol) was dissolved in the mixture of dioxane (8 ml), water (8 ml) and triethylamine (4 ml). BOC-ON (0.85 g, 3.5 mmol) was added and the mixture was stirred under argon at room temperature overnight. Water (30 ml) was added, then the mixture was acidified with 10% citric acid to pH=4. The product was extracted with ethyl acetate (3×30 ml). The organic phase was dried ($MgSO_4$) and evaporated. The residue was purified by column chromatography on silica gel, eluted with dichloromethane-methanol to afford colourless foam (0.54 g, 72%).

$^1$H NMR (DMSO-$d_6$) δ8.8 (1H, s), 7.7 (2H, m), 7.6 (1H, s), 7.5 (2H, m), 7.3 (1H, m), 6.6 (1H, m), 3.3 (2H, m), 1.4 (9H, s), 1.3 (3H, s).

b. N-t-Butyloxycarbonyl-L-2-methyl-3-(2-naphthyl)alanyl-β-O-benzyl-L-aspartyl-L-phenylalaninamide N-t-Butyloxycarbonyl-β-O-benzyl-L-aspartyl-L-phenylalaninamide (0.24 g, 0.5 mmol) was dissolved in trifluoroacetic acid (3 ml) and the solution was kept at room temperature for 1 hr. The trifluoroacetic acid was removed in vacuo, the residue was dissolved in dry dichloromethane (5 ml). N,N-Diisopropylethylamine (0.26 ml, 1.5 mmol), N-t-butyloxycarbonyl-L-2-methyl-3-(2-naphthyl)alanine (0.16 g, 0.5 mmol), and benzotriazole-1-yl-oxy-tris-(dimethylamino)-phosphoniumhexafluorophosphate (BOP reagent) (0.22 g, 0.5 mmol) were added. The solution was stirred at room temperature overnight. The solvent was evaporated, the residue was dissolved in ethyl acetate (20 ml), washed with 5% $KHSO_4$ (3×20 ml), saturated $NaHCO_3$ (2×20 ml) and brine (20 ml). The organic phase was dried (MgSO4) and evaporated. The crude material was purified by column chromatography on silica gel, eluted with dichloromethane-methanol to afford colourless oil (0.27 g, 80%).

$^1$H NMR (DMSO-$d_6$) δ8.3 (1H, d), 7.9-6.9 (21H, m), 5.1 (2H, s), 4.5 (1H, m), 4.3 (1H, m), 3.4-2.7 (6H, m), 1.4 (9H, s), 1.2 (3H, s).

c. N-t-Butyloxycarbonyl-L-tryptophyl-L-2-methyl-3-(2-naphthyl)alanyl-β-O-benzyl-L-aspartyl-L-phenylalaninamide N-t-Butyloxycarbonyl-L-2-methyl-3-(2-naphthyl)alanyl-β-O-benzyl-L-aspartyl-L-phenylalaninamide (0.22 g, 0.3mmol) was dissolved in trifluoroacetic acid (3 ml) and the solution was kept at room temperature for 1 hr. The trifluoroacetic acid was removed in vacuo, the residue was dissolved in dry dichloromethane (5 ml). N,N-Diisopropylethylamine (0.17 ml 1.0 mmol), N-t-butyloxycarbonyl-L-tryptophan (0.10 g, 0.3 mmol) and benzotriazole-1-yl-oxy-tris-(dimethylamino)phosphonium hexafluorophosphate (BOP reagent) (0.13 g, 0.3 mmol) were added. The solution was stirred at room temperature overnight. The solvent was evaporated, the residue was dissolved in ethyl acetate (20 ml), washed with 5% $KHSO_4$ (3×20 ml), saturated $NaHCO_3$ (2×20 ml) and brine (20 ml). The organic phase was dried ($MgSO_4$) and evaporated. The crude material was purified by column chromatography on silica gel, eluted with dichloromethane-methanol to afford colourless oil (0.20 g, 77%). Found: C, 69.01; H, 6.13; N, 9.97%. $C_{50}H_{54}N_6O_8$ requires C, 69.27; H, 6.28; N, 9.67. $^1$H NMR (DMSO-$d_6$) δ10.8 (1H, s), 8.2-6.9 (28H, m), 5.0 (2H, s), 4.5 (1H, m), 4.4 (1H, m), 4.2 (1H, m), 3.3-2.6 (8H, m), 1.25 (3H, s), 1.2 (9H, s).

d. N-t-Butyloxycarbonyl-L-tryptophyl-L-2-methyl-3-(2-naphthyl)alanyl-L-aspartyl-L-phenylalaninamide N-t-Butyloxycarbonyl-L-tryptophyl-L-2-methyl-3-(2-naphthyl)alanyl-β-O-benzyl-L-aspartyl-L-phenylalaninamide (0.17 g, 0.2 mmol) was dissolved in methanol (10 ml), and 10% palladium on activated carbon catalyst (0.03 g) was added. The air was displaced by a slow stream of nitrogen, then hydrogen. The catalyst was kept in suspension by vigorous stirring. The mixture was kept under hydrogen overnight. The catalyst was filtered, washed with methanol (10 ml). The filtrate was evaporated under reduced pressure to afford white solid (0.12 g, 88%), m.p.: 128°–132°, $[\alpha]_D$ −24.5° (c=1.0 in DMSO), Found: C, 61.04; H, 6.13; N, 9.72. $C_{43}H_{48}N_6O_8$. 3.8 mol $H_2O$ requires C, 61.16; H, 6.62; N, 9.95%. $^1H$ NMR (DMSO-$d_6$) δ10.8 (1H, s), 8.3-6.8 (23H, m), 4.3 (2H, m), 4.2 (1H, m), 3.4-2.8 (8H, m), 1.3 (12H, s).

EXAMPLE 58

Preparation of
N-t-Butyloxycarbonyl-L-tryptophyl-L-2-methyl-3-(2-naphthyl)alanyl-L-aspartyl-4-methoxyphenethylamide The compound was prepared essentially as in example 57 except that N-t-butyloxycarbonyl-β-O-benzyl-L-aspartyl-4-methoxyphenethylamide was used instead of N-t-butyloxycarbonyl-β-O-benzyl-L-aspartyl-L-phenylalaninamide in step b. M.p. 120°–30°, $[\alpha]_D$ −18.5° (c=1.0 in methanol), Found C, 64.33; H, 6.48; N, 8.59. $C_{43}H_{49}N_5O_8$. 2.0 mol $H_2O$ requires C, 64.53; H, 6.68; N, 8.75%. $^1H$ NMR (DMSO-$d_6$) δ10.8 (1H, s), 8.2-6.8 (20H, m), 4,4 (1H, m), 4.2 (1H, m), 3.7 (3H, s), 3.3-2.4 (10H, m), 1.3 (3H, s), 1.2 (9H, s).

EXAMPLE 59

Preparation of
N-t-Butyloxycarbonyl-L-tryptophyl-N-methyl-L-3-(2-naphthyl)alanyl-L-aspartyl-4-methoxyphenethylamide a. N-t-Butyloxycarbonyl-L-3-(2-naphthyl)alanine L-3-(2-naphthyl)alanine (0.43 g, 2.0 mmol) was dissolved in the mixture of dioxane (8 ml), water (8 ml) and triethylamine (4 ml). BOC-ON (0.49 g , 2.0 mmol) was added and the mixture was stirred under argon at room temperature overnight. Water (30 ml) was added, and the solution was extracted with ethyl acetate (3×20 ml). The aqueous layer was acidified to pH=4 (10% citric acid) and extracted with ethyl acetate (3×20 ml). The organic phase was dried (MgSO₄) and evaporated to afford colourless oil (0.52 g, 82%). $^1H$ NMR (DMSO-$d_6$) δ7.8 (3H, m), 7.7 (1H, s), 7.4 (3H, m), 7.15 (1H, d), 4.2 (1H, m), 3.2 (1H, m), 2.9 (1H, m), 1.3 (9H, s).

b. N-Methyl-N-t-butyloxycarbonyl-L-3-(2-naphthyl)alanine

N-t-Butyloxycarbonyl-L-3-(2-naphthyl)alanine (0.39 g, 1.2 mmol) was dissolved in anhydrous tetrahydrofuran. The solution was cooled to 0° C. and stirred under nitrogen. Iodomethane (0.6 ml 10 mmol), then sodium hydride (60% dispersion in mineral oil, 0.14 g, 3.6mmol) were added. The mixture was stirred at room temperature for 24 hrs. Ethyl acetate (3 ml), then water (1 ml) were added dropwise. The solvents were evaporated under reduced pressure, and the residual oil was partitioned between diethyl ether (20 ml) and water (30 ml). The organic layer was washed with saturated NaHCO₃ (20 ml). The combined aqueous extracts were acidified to pH=2 (1N HCl). The product was extracted with ethyl acetate (2×20 ml), washed with water (2×20 ml), 5% NaHSO₃ (2×20 ml), then water (20 ml). The organic phase was dried (MgSO₄) and evaporated to afford colourless oil (0.39 g, 96%). $^1H$ NMR (DMSO-$d_6$) (mixture of rotamers) δ7.8 (3H, m), 7.7 (1H, s), 7.4 (3H, m), 4.9 and 4.7 (1H, m), 3.3 (2H, m), 3.0 and 2.6 (3H, s), 1.2 and 1.1 (9H, s).

c. N-Methyl-N-t-butyloxycarbonyl-L-3-(2-naphthyl)alanineN-hydroxysuccinimide ester A solution of N-methyl-N-t-butyloxycarbonyl-L-3-(2-naphthyl)alanine (0.35 g, 1.1 mmol) and N-hydroxysuccinimide (0.12 g, 1.1 mmol) in dry 1,2-dimethoxyethane (5.0 ml) was cooled in an ice-water bath. Dicyclohexylcarbodiimide (0.22 g, 1.1 mmol) was added. The mixture was stirred at 5° C. overnight. The precipitated N,N-dicyclohexylurea was removed by filtration and the solvent was evaporated in vacuo to afford a colourless oil (0.43 g). $^1H$ NMR (DMSO-$d_6$) (mixture of rotamers) δ7.8 (4H, m), 7.4 (3H, m), 5.5 and 5.3 (1H, m), 3.4 (2H, m), 2.8 (4H, s), 2.7 (3H, s), 1.2 (9H, s).

d. N-Methyl-N-t-butyloxycarbonyl-L-3-(2-naphthyl)alanyl-β-O-benzyl-L-aspartyl-4-methoxyphenethylamide N-t-Butyloxycarbonyl-β-O-benzyl-L-aspartyl-4-methoxyphenethylamide (0.46 g, 1.0 mmol) was dissolved in trifluoroacetic acid (3 ml) and the solution was kept at room temperature for 1 hr. The trifluoroacetic acid was removed in vacuo, the residue was dissolved in dry 1,2-dimethoxyethane (5 ml), triethylamine (0.4 ml, 3.0 mmol) and N-Methyl-N-t-butyloxycarbonyl-L-3-(2-naphthyl)alanine N-hydroxysuccinimide ester (0.43 g, 1.0 mmol) dissolved in 1,2-dimethoxyethane (3 ml) were added. The mixture was stirred at room temperature overnight, then diluted with water (20 ml). The 1,2-dimethoxyethane was evaporated in vacuo and the product was extracted with ethyl acetate (2×20 ml). The organic phase was dried (MgSO₄) and evaporated. The crude product was purified by column chromatography on silica gel, eluted with dichloromethane-methanol to afford colourless foam (0.62 g, 92%). $^1H$ NMR (DMSO-$d_6$) (mixture of rotamers) δ8.2 (1H, d), 7.8 (3H, m), 7.7 (1H, s), 7.4 (3H, m), 7.3 (5H, s), 7.1 (2H, d), 6.8 (2H, d), 5.1 (2H, s), 4.9 (1H, m), 4.7 (1H, m), 3.7 (1H, s), 3.3-2.6 (8H, m), 2.6 (3H, 2s), 1.1 and 1.0 (9H, s).

e. N-t-Butyloxycarbonyl-L-tryptophyl-N-methyl-L-3-(2-naphthyl)alanyl-β-O-benzyl-L-aspartyl-4-methoxyphenethylamide N-Methyl-N-t-butyloxycarbonyl-L-3-(2-naphthyl)alanyl-β-O-benzyl-L-aspartyl-4-methoxyphenethylamide (0.53 g, 0.8mmol) was dissolved in trifluoroacetic acid (3 ml) and the solution was kept at room temperature for 1 hr. The trifluoroacetic acid was removed in vacuo, the residue was dissolved in dry dichloromethane (8 ml). N,N-Diisopropylethylamine (0.42 ml 2.4 mmol), N-t-butyloxycarbonyl-L-tryptophan (0.24 g, 0.8 mmol) and bromo-tris-pyrrolidinophosphonium hexafluorophosphate (PyBrop reagent) (0.37 g, 0.8 mmol) were added. The solution was stirred at room temperature for 1 hr. The solvent was evaporated, the residue was dissolved in ethyl acetate (20 ml), washed with 5% KHSO₄ (3×20 ml), saturated NaHCO₃ (2×20 ml) and brine (20 ml). The organic phase was dried (MgSO₄) and evaporated. The crude .material was purified by column chromatography on silica gel, eluted with dichloromethane-methanol to afford colourless oil (0.38 g, 55%). $^1H$ NMR (mixture of rotamers) δ10.8 (1H, m), 8.4-6.7 (24H, m), 5.3 (1H, m), 5.0 (2H, s), 4.6 (1H, m), 4.4 (1H, m), 3.7 (3H, s), 3.4-2.5 (13H, m), 1.2 and 1.15 (9H, s).

f. N-t-Butyloxycarbonyl-L-tryptophyl-N-methyl-L-3-(2- naphthyl)alanyl-L-aspartyl-4-methoxyphenethylamide

N-t-Butyloxycarbonyl-L-tryptophyl-N-methyl-L-3-(2-naphthyl)alanyl-β-O-benzyl-L-aspartyl-4-methoxyphenethylamide (0.26 g, 0.3 mmol) was dissolved in methanol (10 ml), and 10% palladium on activated carbon catalyst (0.03 g) was added. The air was displaced by a slow stream of nitrogen, then hydrogen. The catalyst was kept in suspension by vigorous stirring. The mixture was kept under hydrogen overnight. The catalyst was filtered, washed with methanol (10 ml). The filtrate was evaporated under reduced pressure and the residual glass was triturated with hexane to afford white solid (0.17 g, 74%), m.p. 115°–20°, $[\alpha]_D$ –54° (c=1.0 in methanol), Found: C, 65.95; H, 6.60; N, 8.83%. $C_{43}H_{49}N_5O_8$. 1.0 mol $H_2O$ requires C, 66.05; H, 6.57; N, 8.96%. $^1H$ NMR (DMSO-$d_6$) (mixture of rotamers) δ10.8 (1H, m), 8.2-6.6 (19H, m), 5.4 (1H, m), 4.5 (2H, m), 3.7 (3H, s), 3.6-2.5 (13H, m), 1.2 and 1.15 (9H, s).

EXAMPLE 60

Preparation of
N-t-Butyloxycarbonyl-L-N$^{in}$-formyltryptophyl-L-3-(2-naphthyl)alanyl-L-aspartyl-L-phenylalaninamide This was prepared essentially as described in example 16 with the exception that N-t-butyloxycarbonyl-L-N$^{in}$-formyltryptophan N-hydroxysuccinimide ester was used in place of N-fluorenylmethoxycarbonyl-L-tryptophan pentafluorophenyl ester in step c., m.p 197°–202°, $[\alpha]_D$ –27.8° (c=0.18 in DMSO), Found C, 62.08; H, 5.37; N, 10.18%; $C_{43}H_{46}N_6O_9$. 0.41 $CHCl_3$ requires C, 62.01; H, 5.56; N, 9.99%; $^1H$ NMR (DMSO-$d_6$) δ9.6 (1H, bs), 9.2 (1H, d), 8.5 (1H, bs), 8.2-6.7 (21H, m), 4.7 (1H, m), 4.6 (1H, m), 4.4 (1H, m), 4.2 (1H, m), 3.1-2.6 (8H, m), 1.2 (9H, s).

EXAMPLE 61

Preparation of
N-t-Butyloxycarbonyl-L-tryptophyl-L-3-(2-naphthyl)alanyl-L-glutamyl-4-methoxyphenethylamide The compound was prepared essentially as in example 1 except that N-t-butyloxycarbonyl-γ-O-benzyl-L-glutamyl-4-methoxyphenethylamide (prepared by coupling N-t-butyloxycarbonyl-γ-O-benzyl-L-glutamic acid N'-hydroxysuccinimide ester with 4-methoxyphenethylamine in DME) was used in place of N-t-butyloxycarbonyl-β-O-benzyl-L-aspartyl-L-phenylalaninamide in step d. m.p. 145°–157°, $[\alpha]_D$ –15° (c=0.49 in DMSO), Found C, 67.66; H, 6.47; N, 9.17%. $C_{43}H_{49}N_5O_8$ requires C, 67.61; H, 6.47; N, 8.98%. $^1H$ NMR (DMSO-$d_6$) δ10.8 (1H, s), 8.4-6.8 (20H, m), 4.6, 4.2, 4.1 each (1H, m), 3.6 (3H, s), 3.5-2.4 (8H, m), 2.2 (2H, t), 1.8 (2H, m), 1.2 (9H, s).

EXAMPLE 62

Preparation of
N-t-Butyloxycarbonyl-L-tryptophyl-L-3-(2-naphthyl)alanyl-L-aspartyl]-3-azaspiro[5.4]decylamide The compound was prepared essentially as in example 26 but using 3-azaspiro [5.4]decylamine instead of 1,2,3,4-tetrahydroisoquinoline in step a. $[\alpha]_D$ –4.8° (c=1.0 in DMSO), Found C, 68.00; H, 7.04; N, 9.20% $C_{42}H_{51}N_5O_7$ requires C, 68.36; H, 6.97; N, 9.49%. $^1H$ NMR (DMSO-$d_6$) δ10.8 (1H, s), 8.5 to 6.7 (15H, m), 4.9 (1H, m), 4.6 (1H, s), 4.1 (1H, s) 3.6 to 2.2 (10H, m), 1.5 (4H, m), 1.2 (9H, s), 1.4-0.8 (8H, m).

EXAMPLE 63

Preparation of
N-t-Butyloxycarbonyl-L-tryptophyl-L-3-(2-naphthyl)alanyl-L-aspartyl-α-2-phenethylester a. N-t-Butyloxycarbonyl-L-tryptophyl-L-3-(2-naphthyl)alanyl-β-O-benzyl-L-aspartyl-α-2-phenethylester An aqueous solution of caesium carbonate (80 mg in 0.6 ml water) was added dropwise to a solution of N-t-butyloxycarbonyl-L-tryptophyl-L-3-( 2-naphthyl)alanyl-β-O-benzyl-L-aspartic acid (319 mg, 0.45 mmol) (prepared as in example 25 step a) in methanol (10 ml) and water (1 ml) until the solution had a pH of 7. The solution was evaporated, dried, and the residue taken up in DMF. Phenethyl bromide (0.95 mg, 0.50 mmol) was added and the mixture stirred at room temperature overnight. The solvent was evaporated and the residue taken up in ethyl acetate then washed sequentially with saturated aqueous sodium bicarbonate, water, 10% aqueous citric acid, water, and brine, dried over anhydrous sodium sulphate and evaporated to yield the crude product (292 mg) which was used without further purification. $^1H$ NMR (DMSO-$d_6$) δ10.8 (1H, s), 8.7 (1H, d), 8.0 (1H, d), 7.9-6.8 (23H, m), 5.1 (2H, s), 4.7 (2H, m), 4.2 (3H, m), 3.3-2.5 (8H, m), 1.2 (9H, s).

b. N-t-Butyloxycarbonyl-L-tryptophyl-L-3-(2-naphthyl)alanyl-L-aspartyl-α-2-phenethylester N-t-Butyloxycarbonyl-L-tryptophyl-L-3-(2-naphthyl)alanyl-β-O-benzyl-L-aspartyl-α-2-phenethylester was hydrogenolysed following the procedure given in example 1, step e, except that no acetic acid was added m.p. 96°–99°, $[\alpha]_D$ –36.4° (c=0.55 in methanol), found C, 68.03; H, 6.29; N, 7.81%. $C_{41}H_{44}N_4O_8$ requires C, 68.32; H, 6.15; N, 7.77%. $^1H$ NMR (DMSO-$d_6$) δ10.8 (1H, s), 8.7 (1H, d), 8.0 (1H, d), 7.9-6.7 (18H, m), 4.7, 4.6, each (1H, m), 4.2 (2H, m), 4.1 (1H, m), 3.3-2.5 (6H, m), 2.8 (2H, t), 1.2 (9H, s).

EXAMPLE 64

Preparation of
N-t-Butyloxycarbonyl-L-tryptophyl-L-3-(2-naphthyl)alanyl-L-aspartyl-3,3-dimethylbutylamide The compound was prepared as in example 25 except that 3,3-dimethylbutylamine was used in place of 1-aminoindane in step c. m.p. 119°–123°, $[\alpha]_D$ –41.9° (c=0.43 in methanol), found C, 65.51; H, 7.09; N, 9.94%. $C_{39}H_{49}N_5O_7$. 0.7 mol $H_2O$ requires C, 65.63; H, 7.14; N, 9.81%. $^1H$ NMR (DMSO-$d_6$) δ 10.8 (1H, s), 8.4 (1H, d), 8.0 (1H, d), 7.9-6.8 (14H, m), 4.7, 4.5, 4.1 each (1H, m), 3.3-2.5 (8H, m), 1.2 (11H, s), 0.8 (9H, s).

EXAMPLE 65

Preparation of
N-t-Butyloxycarbonyl-L-tryptophyl-L-3-(2-naphthyl)alanyl-L-aspartyl-3-fluorophenethylamide The compound was prepared as in example 25 except that 3-fluorophenethylamine was used in place of 1-aminoindane in step c. m.p. 120°–124°, $[\alpha]_D$ –22.4° (c=0.49 in methanol) found C, 61.12; H, 5.68; N, 8.56%. $C_{41}H_{44}FN_5O_7$. 1.1 mol $SiO_2$ requires C, 61.26; H, 5.52; N, 8.71%. $^1H$ NMR (DMSO-$d_6$) δ10.8 (1H, s), 8.4 (1H, d), 8.0 (1H, d), 7.9-6.8 (18H, m), 4.7, 4.5, 4.2 each (1H, m), 3.2 (2H, m), 3.3-2.3 (6H, m), 2.7 (2H, t), 1.2 (9H, s).

Biological data

The compounds were assayed for gastrin activity using the mouse stomach assay as described by Black, J. W. and Shankley, N. P., Br. J. Pharmacol., 86, 571–579, (1985), and also in the guinea-pig fundus assay, as follows:

The stomach is removed from a male Dunkin-Hartley guinea-pig (250–500 g), and Krebs solution is injected through a hypodermic needle under the top stomach muscle layer. The composition (mM) of the Krebs solution is as follows: $Na^+$ 143, $K^+$ 5.9, $Ca^{2+}$ 2.5, $Mg^{2+}$ 1.2, $Cl^-$ 128, $H_2PO_4^-$ 2.2, $HCO_3^-$ 24.9, $SO_4^{2-}$ 1.2, dextrose 10. Strips of muscle (approximately 2.5 cm by 1 cm) are removed from the proximal area of the stomach (one from each side) and tied with cotton thread to isotonic transducers under an initial loading tension of 0.35 g.

The preparation is immersed in 20 mls of Krebs solution containing $10^{-8}$M devazepide (25 μl $2\times10^{-3}$M devazepide/ 100% DMF solution in 5 dm$^3$ Krebs) and gassed with 95% $O_2/5\%$ $CO_2$. The function of the devazepide is to block possible effects at CCK receptors present in the tissue.

The preparation is washed twice over a 60 minute period then 10 mM KCl is added. At 90 minutes, test compounds (ie. potential antagonists) are added and a further 60 minute equilibration period allowed. After this time, cumulative agonist (e.g. pentagastrin) dose-response curves are constructed.

The results of the two assays are shown in Tables 1 and 2. Data are given only where the compound has significant activity in the relevant assay.

TABLE 1

| Compound of Example | pK$_B$ mouse stomach | Acid seretion at $10^{-5}$M test compound, relative to pentagastrin (%) |
| --- | --- | --- |
| 1 | 6.2 | 65 |
| 2 | 5.6 | 20 |
| 5 | 5.6 | 23 |
| 6 | 5.6 | 22 |
| 7 | 5.7 | NS |
| 8 | 5.9 | 28 |
| 10 | 6.0 | NS |
| 11 | 6.6 | 60 |
| 16 | 5.7 | 67 |
| 17 | 5.9 | 44 |
| 18 | 5.8 | 54 |
| 19 | 5.3 | 80 |
| 20 | 6.2 | 33 |
| 23 | 5.5 | 40 |
| 24 | 6.6 | 50 |
| 31 | 5.0 | 40 |
| 33 | 5.2 | NS |
| 34 | 6.5 | 40 |
| 40 | 5.2 | 22 |
| 42 | 5.2 | 30 |
| 46 | 5.6 | NS |
| 47 | 5.5 | 25 |
| 52 | 5.6 | 25 |
| 54 | 5.4 | 25 |
| 56 | 5.6 | NS |
| 59 | 5.3 | 20 |
| 60 | 5.3 | 20 |
| 65 | 5.3 | NS |

(NS = not significant)

TABLE 2

| Example | pK$_B$ |
| --- | --- |
| 1 | 5.5 |
| 2 | 5.9 |
| 3 | 5.6 |
| 4 | 5.8 |

TABLE 2-continued

| Example | pK$_B$ |
| --- | --- |
| 6 | 5.6 |
| 7 | 5.3 |
| 8 | 5.0 |
| 9 | 5.6 |
| 10 | 5.9 |
| 12 | 5.5 |
| 15 | 5.3 |
| 18 | 5.9 |
| 19 | 5.8 |
| 25 | 5.7 |
| 26 | 5.5 |
| 27 | 5.8 |
| 29 | 6.0 |
| 30 | 5.7 |
| 31 | 6.1 |
| 32 | 6.1 |
| 33 | 6.2 |
| 34 | 5.8 |
| 36 | 5.4 |
| 38 | 5.9 |
| 39 | 5.4 |
| 40 | 5.8 |
| 41 | 6.0 |
| 42 | 5.3 |
| 44 | 6.0 |
| 46 | 6.0 |
| 47 | 5.8 |
| 48 | 5.7 |
| 49 | 6.2 |
| 51 | 5.7 |
| 52 | 5.9 |
| 54 | 6.2 |
| 56 | 5.5 |
| 57 | 5.6 |
| 61 | 5.7 |
| 62 | 5.6 |
| 63 | 5.9 |
| 64 | 5.9 |
| 65 | 6.1 |

Standard errors estimated for the values of pK$_B$ were all less than 5%.

The compounds of the invention were also assayed for CCK-antagonist activity as follows:

Isolated, strip preparations were prepared from gall-bladders removed from male Dunkin-Hartley guinea-pigs (250–500 g body weight) according to the method of La Morte, W. W., et al., J.P.E.T., 217, (3), 638–644 (1981).

The complete gall-bladder is removed and opened along the longitudinal axis. Strips measuring 3 mm in the longitudinal axis and 1 mm in the transverse axis are cut and then tied with cotton to stainless steel wires. The preparation is connected to a GRASS FTO3 isometric transducer under an initial loading tension of 1 g and is immersed in 20 mls of Krebs solution maintained at 37° C. and gassed with 95% $O_2/5\%$ $CO_2$. The Krebs solution is as detailed above in connection with the fundus assay, except that the $Ca^{2+}$ concentration is decreased to 0.5 mM. After 30 mins the preparation is washed. Drug addition begins after an initial 90 min stabilisation period. Responses are measured as changes in tension from that immediately prior to any drug addition. Single cumulative agonist concentration-effect curves, using CCK-8 as agonist, are obtained on each preparation in the absence and presence of test compound which has been incubated for 60 minutes. The antagonist activity of the test compound is estimated and expressed as the negative logarithm (base 10) of the equilibrium dissociation constants (pK$_B$) using the modifications of standard competitive analysis described by Black et al., Br. J. Pharmacol.,86,571–579, (1985) and Shankley et al., Br. J. Pharmacol.,94,264–274 (1988).

The results are shown in Table 3.

TABLE 3

| Example | $pK_B$ |
|---|---|
| 1 | 5.3 |
| 2 | 6.9 |
| 5 | 5.4 |
| 7 | 5.8 |
| 9 | 5.9 |
| 10 | 7.2 |
| 11 | 5.9 |
| 12 | 7.4 |
| 13 | 5.9 |
| 14 | 6.0 |
| 15 | 6.2 |
| 16 | 5.6 |
| 17 | 5.5 |
| 18 | 6.2 |
| 19 | 6.3 |
| 20 | 6.7 |
| 21 | 6.2 |
| 22 | 6.2 |
| 23 | 5.9 |
| 24 | 6.5 |
| 25 | 6.3 |
| 26 | 6.6 |
| 27 | 6.5 |
| 28 | 6.4 |
| 29 | 5.9 |
| 30 | 6.6 |
| 31 | 6.5 |
| 32 | 6.6 |
| 33 | 7.0 |
| 34 | 6.9 |
| 35 | 5.8 |
| 36 | 6.3 |
| 37 | 6.4 |
| 38 | 7.1 |
| 39 | 6.7 |
| 40 | 7.1 |
| 41 | 6.5 |
| 42 | 6.0 |
| 43 | 6.5 |
| 44 | 6.2 |
| 45 | 6.1 |
| 46 | 6.5 |
| 47 | 6.7 |
| 48 | 6.6 |
| 49 | 6.8 |
| 50 | 6.1 |
| 51 | 7.0 |
| 52 | 6.4 |
| 53 | 6.6 |
| 54 | 6.4 |
| 55 | 6.4 |
| 56 | 7.2 |
| 57 | 6.0 |
| 59 | 6.7 |
| 60 | 6.4 |
| 61 | 6.5 |
| 63 | 7.0 |
| 64 | 7.0 |
| 65 | 6.7 |

As before, standard errors were all estimated to be less than 5%.

We claim:

1. A compound of the formula:

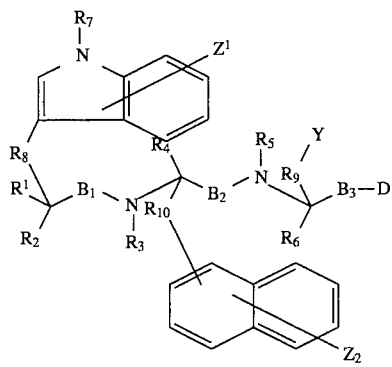

wherein $R_1$ is H or

$R_2$, $R_3$, $R_4$, $R_5$, and $R_6$ are independently H or methyl, $R_7$ is H, methyl, ethyl, benzyl or formyl, $R_8$ and $R_{10}$ are independently $C_1$ to $C_3$ alkylene or are absent, $R_9$ is $C_1$ to $C_3$ alkylene or is linked to $R_6$ to form a 3- to 6-membered cycloalkyl group or is absent $R_{11}$ is an N-blocking group and $R_{12}$ is H or methyl, or $R_{11}$ and $R_{12}$ are linked to form an N-blocking group $B_1$, $B_2$ and $B_3$ are independently —$CH_2$— or a carbonyl group, Y is —$CO_2H$, tetrazole or $CONR_{13}R_{14}$ (wherein $R_{13}$ and $R_{14}$ are independently H or $C_1$ to $C_6$ hydrocarbyl)

$Z_1$ and $Z_2$ (which may be the same or different) are optional and each represents one or more substituents in the aromatic ring system, such substituents being independently selected from $C_1$ to $C_6$ alkyl (two such alkyl substituents optionally forming a ring fused to one or both of the aromatic rings), $C_1$ to $C_6$ alkoxy, $C_1$ to $C_6$ thioalkoxy, carboxy, $C_1$ to $C_6$ carboalkoxy, nitro, trihalomethyl, hydroxy, —$NR_{15}R_{16}$ (wherein $R_{15}$ and $R_{16}$ are independently H or $C_1$ to $C_6$ alkyl ), $C_1$ to $C_6$ alkylaryl, $C_1$ to $C_6$ alkyl (substituted aryl), halo, sulphonamide and cyano and D is —O—$R_{17}$—Q or

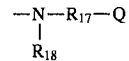

(wherein Q is H or a carbocyclic or heterocyclic group which may optionally be substituted; $R_{17}$ is absent or is $C_1$ to $C_{10}$ hydrocarbylene, optionally substituted by —OH, —SH, halogen, —$CO_2R_{19}$ or —$CONR_{19}R_{20}$ (wherein $R_{19}$ and $R_{20}$ are independently H or $C_1$ to $C_6$ hydrocarbyl), and optionally having up to three carbon atoms replaced by —O—, —S— or —$NR_{21}$— (wherein $R_{21}$ is H or an N-blocking group), provided that $R_{17}$ contains at least one carbon atom if Q is H and that $R_{17}$ does not contain —O—O—; and $R_{18}$ is H or $C_1$ to $C_6$ alkyl or forms an alkylene (e.g. $C_1$ to $C_4$ alkylene) link to Q) or a pharmaceutically acceptable salt thereof.

2. A compound according to claim 1, wherein $Z_1$ is absent.

3. A compound according to claim 1 wherein $Z_2$ is absent.

4. A compound according to claim 1 wherein $R_{11}$ is a group of the formula $R_{22}-X_1-(-N(R_{23})-R_{24}-X_2)_r-$, wherein $X_1$ and $X_2$ are independently $-C(O)-$, $-O-C(O)-$, $-SO-$, or $-SO_2-$ $R_{22}$ is $C_1$ to $C_{20}$ hydrocarbyl, optionally substituted by $C_1$ to $C_6$ alkoxy, $C_1$ to $C_6$ thioalkoxy, halo, nitro, or tri($C_1$ to $C_3$ alkyl)silyl, $R_{23}$ is H or is linked to $R_{22}$, $R_{24}$ is $C_1$ to $C_3$ hydrocarbylene, and r is 0 or 1.

5. A compound according to claim 1 wherein $R_{12}$ is a $-C(O)-$ group linked to $R_{11}$.

6. A compound according to claim 1 wherein Q is selected from the group consisting of phenyl, naphthyl, indanyl, fluorenyl, (1,2,3,4)-tetrahydronaphthyl, indenyl, isoindenyl, cyclohexyl, adamantyl and pyridyl, and substituted derivatives thereof.

7. A compound according to claim 1 wherein Q has from one to three substituents independently selected from the group consisting of $C_1$ to $C_6$ alkyl, $C_1$ to $C_6$ alkoxy, $C_1$ to $C_6$ thioalkoxy, carboxy, $C_1$ to $C_6$ carboalkoxy, nitro, trihalomethyl, hydroxy, $-NR_{25}R_{26}$ (wherein $R_{25}$ and $R_{26}$ are independently H or $C_1$ to $C_6$ alkyl), aryl, substituted aryl, $C_1$ to $C_6$ alkylaryl, $C_1$ to $C_6$ alkyl(substituted aryl), halo, sulphonamide and cyano.

8. A compound according to claim 7 wherein said substituents are independently selected from the group consisting of $C_1$ to $C_6$ straight chain alkyl, $C_1$ to $C_6$ straight chain alkoxy, $C_1$ to $C_6$ straight chain thioalkoxy, carboxy, $C_1$ to $C_6$ straight chain carboalkoxy, nitro, trihalomethyl, hydroxy, $-NR_{25}R_{26}$ (wherein $R_{25}$ and $R_{26}$ are independently H or $C_1$ to $C_6$ straight chain alkyl), $C_1$ to $C_6$ straight chain alkylaryl, $C_1$ to $C_6$ straight chain alkyl(substituted aryl), halo, sulphonamide and cyano.

9. A compound according to claim 1 wherein Q is phenyl or substituted phenyl.

10. A compound according to claim 1 wherein the asymmetric carbon atoms to which $R_2$ and $R_4$ are attached are in the L configuration.

11. A compound according to claim 1 wherein D is

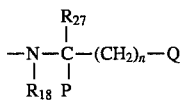

and wherein $R_{18}$ is H or methyl, $R_{27}$ is H or methyl, or is an alkylene chain linked to Q, n is from 0 to 3, and P is H, $-CH_2OH$, $-CO_2R_{19}$ or $-CONR_{19}R_{20}$ (wherein $R_{19}$ and $R_{20}$ are independently H or $C_1$ to $C_6$ alkyl).

12. A compound according to claim 11, wherein the carbon atom to which $R_{27}$ is attached is asymmetric and is in the L configuration.

13. A compound according to claim 1 wherein $R_{17}$ is absent.

14. A compound according to claim 1 wherein $B_3$ is carbonyl when D is $-O-R_{17}-Q$.

15. A compound according to claim 1 wherein $B_1$, $B_2$ and $B_3$ are each carbonyl.

16. N-t-butyloxycarbonyl-L-tryptophyl-L-3-(2-naphthyl)alanyl-D-aspartyl-L-phenylalaninamide, a compound according to claim 1.

17. A pharmaceutical composition comprising a compound according to claim 1 together with a pharmaceutically acceptable diluent or carrier.

18. A method of preparing a compound according to claim 1, said method comprising the step of coupling a suitably protected compound of the formula

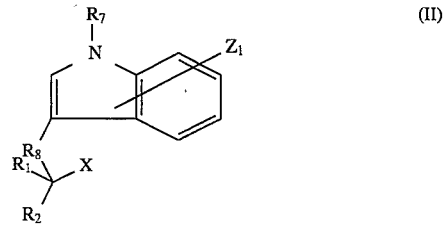

with a suitably protected compound of the formula

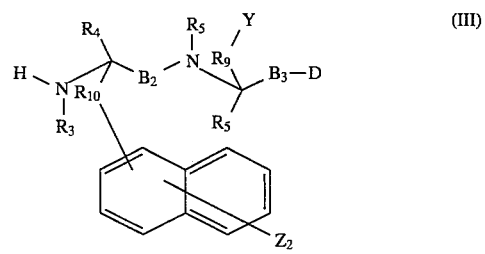

wherein $R_1$, $R_2$, $R_3$, $R_4$, $R_5$, $R_6$, $R_7$, $R_8$, $R_9$, $R_{10}$, $Z_1$, $Z_2$, Y, D, $B_2$ and $B_3$ are as defined in claim 1, and X is $-COOH$ or $-CHO$, said method comprising the further step of reducing the resulting Schiff base when X is $-CHO$.

19. A method according to claim 18 wherein the compound of formula III is prepared by coupling a suitably protected compound of the formula

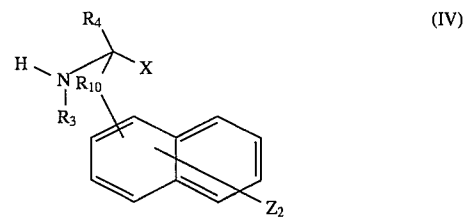

with a suitably protected compound of the formula

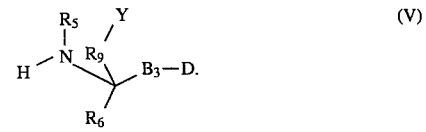

20. A method according to claim 19, wherein D is $-N(R_{18})R_{17}-Q$ and the compound of formula V is prepared by coupling a suitably protected compound of the formula

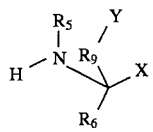
(VI)

wherein X is —COOH or —CHO, with a suitably protected compound of the formula H-D, said method comprising the further step of reducing the resulting Schiff base when X is —CHO.

21. A method according to claim 19, wherein D is —O—$R_{17}$—Q and the compound of formula V is prepared by coupling a suitably protected compound of formula VI, wherein X is —COO⁻, with a suitably protected compound of the formula Br—$R_{17}$—Q.

22. A method of preparing a compound of formula I according to claim 1, said method comprising the step of coupling a suitably protected compound of the formula

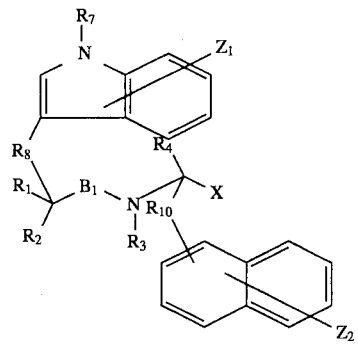
(VII)

with a suitably protected compound of formula V, wherein $R_1$, $R_2$, $R_3$, $R_4$, $R_5$, $R_6$, $R_7$, $R_8$, $R_9$, $R_{10}$, $Z_1$, $Z_2$, Y, D, $B_1$ and $B_3$ are as defined in claim 1, and X is —COOH or —CHO, said method comprising the further step of reducing the resulting Schiff base when X is —CHO.

23. A method of preparing a compound of formula I according to claim 1, said method comprising the step of coupling a suitably protected compound of the formula

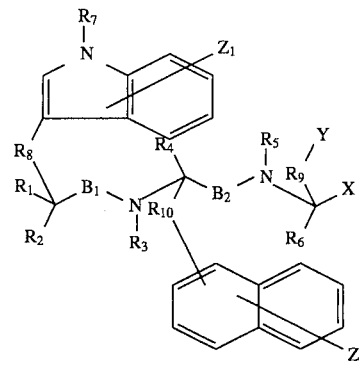
(VIII)

wherein $R_1$, $R_2$, $R_3$, $R_4$, $R_5$, $R_6$, $R_7$, $R_8$, $R_9$, $R_{10}$, $Z_1$, $Z_2$, Y, $B_1$ and $B_2$ are as defined in claim 1 and X is —COOH or —CHO, with a suitably protected compound of the formula H-D, wherein D is as defined in claim 1, said method comprising the further step of reducing the resulting Schiff base when X is —CHO.

24. A method of preparing a compound of formula I according to claim 1, said method comprising the step of coupling a suitably protected compound of formula VIII,

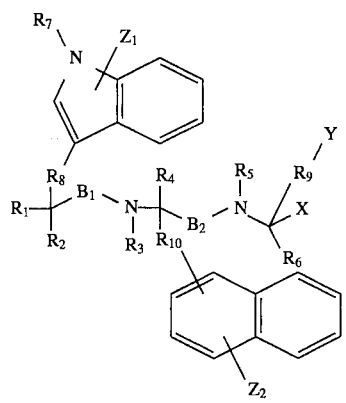

wherein $R_1$, $R_2$, $R_3$, $R_4$, $R_5$, $R_6$, $R_7$, $R_8$, $R_9$, $R_{10}$, $Z_1$, $Z_2$, Y, $B_1$ and $B_2$ are as defined in claim 1 and X is —COO, with a suitably protected compound of the formula Br—$R_{17}$—Q, wherein $R_{17}$ and Q are as defined in claim 1.

* * * * *